United States Patent [19]
Donovan et al.

[11] Patent Number: 5,874,587
[45] Date of Patent: Feb. 23, 1999

[54] IMIDAZOLIUM CATIONS, PROCESSES FOR THEIR PREPARATION, AND USES THEREFOR

[75] Inventors: Robert J. Donovan, Center Morchias; Robert J. Morgan, New Hyde Park, both of N.Y.

[73] Assignee: The Rockefeller University, New York, N.Y.

[21] Appl. No.: 673,687

[22] Filed: Jun. 25, 1996

[51] Int. Cl.[6] .................. C07D 233/54; C07D 293/00; C07D 233/00; C07D 345/00
[52] U.S. Cl. .................... 548/335.1; 540/1; 548/100; 548/300.1; 548/301.7
[58] Field of Search .................. 540/1; 548/100, 548/300.1, 301.7, 335.1

[56] References Cited

U.S. PATENT DOCUMENTS 5,470,502  11/1995  Hahn et al. .................. 252/301.35
5,501,927   3/1996  Imai et al. .................. 430/78

OTHER PUBLICATIONS

Armstrong et al., Acc. Chem. Res., 1966, 29. pp. 123–131.
Ashton et al. (1996) Chem. Eur. J. 31–.
Bakthavalam et al., J. Med. Chem., (1991), 34, 3235–41.
Balzani et al. (1996) Chem. Rev. 96:759–833.
Juris et al. (1988) Coordin. Chem. Rev. 84:85–277.
Chao et al. (1996) Nature 380:396–7.
Czarnik, A.W. (1996) Acc. Chem. Res. 29:112–3.
DeWitt et al. (1996) Acc. Chem. Res. 29:114–22.
Ellman, Acc. Chem. Res., 1996, 29 pp. 132–143.
Fabbrizzi et al., Chem. Euro. J., (1996), 2, pp. 75–(et seq.).
Gordon et al., Acc. Chem. Res., 1996, 29, pp. 144–154.
Guttmann et al. (1982) Antimicrob. Agents Chemother. 22:128–36.
Hsieh–Wilson et al. (1996) Acc. Chem. Res. 29:164–70.
Kröhnke, F. (1976) Synthesis, Jan.:1–24.
Kraus et al., Chem. Rev., (1996), 96, 523–527.
Marder et al., Science, (1994) 263, pp. 1706–1715.
Rich et al., J. Am. Chem. Soc., (1995), 117, 733–9.
Still, W. C. (1996) Acc. Chem. Res. 29:155–63.
Stoddart et al. (1996) Chem. Eur. J. 2:32–.
Tsien, R.Y. (1994) Chem. Eng. News, Jul. 18, pp. 34–44.
Tyagi et al., Nature Biotechnology, 14, pp. 303–308.
Wilchek et al., Analytical Biochemistry, (1988), 171, 1–32.
Yamamoto et al. (1996) J. Am. Chem. Soc. 118:3930–7.
Yitzchaik et al. (1996) Acc. Chem. Res. 29:197–202.

*Primary Examiner*—Ardin H. Marschel
*Assistant Examiner*—Jezia Riley
*Attorney, Agent, or Firm*—Klauber & Jackson

[57] ABSTRACT

Novel imidazolium compounds of the formula

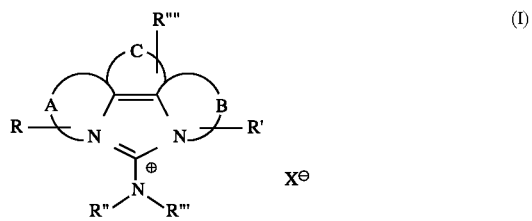

wherein A represents the atomic group necessary to form a heteroaromatic ring, which may be optionally substituted by one or more R substituents selected from the group consisting of aryl, heteroaryl, lower alkyl, hydroxy, halide, or carboxy substitutents; B is an optional substituent which represents the atomic group necessary to form a heteroaromatic ring or a double or triple carbon-nitrogen bond, which may optionally be substituted by one or more R' substituents selected from the group consisting of aryl, heteroaryl, lower alkyl, hydroxy, halide, or carboxy substitutents; C is an optional substituent which represents the atomic group necessary to form an aromatic or heteroaromatic ring, which may optionally be substituted by one or more R"" substituents selected from the group consisting of aryl, heteroaryl, lower alkyl, hydroxy, halide, or carboxy substituents; R" and R'" are each independently a lower alkyl or aryl group, or together with the nitrogen atom to which they are attached, form a heterocyclic ring having from 5 to 7 members, which may optionally contain a sulfur, oxygen, silicon, selenium or an additional nitrogen atom; and X is an anion; are useful in a variety of industrial and medical applications.

39 Claims, 8 Drawing Sheets

41

20

21

100

101

52

54

63

64

42

43

80

82

84

85

87

Monomer ———
Dimer ..........

IMIDAZOLIUM CATIONS, PROCESSES FOR THEIR PREPARATION, AND USES THEREFOR

BACKGROUND OF THE INVENTION

This invention relates generally to the preparation of novel imidazolium cations, processes for such preparation, and various methods of use for the compounds of the invention.

The Vilsmeier-Haack reaction has been an established method for the formylation of aromatic rings. Such formylation however is applicable mainly to active substrates, such as amines and phenols, and aromatic hydrocarbons which are much more active than benzene such as azulenes and ferrocenes. Typically, POCl₃ and dimethylformamide are used as the reactants, although other dialkyl amides have been used as well. It is also widely used as a method for chlorinating, especially with thionyl chloride, under similar reaction conditions.

OBJECTS OF THE INVENTION

It is an object of the present invention to provide novel imidazolium cations, and salts thereof, which have a variety of utilities.

It is a further object of the present invention to provide processes for the preparation of the aforesaid imidazolium cations and their salts under favorable conditions in large quantities.

A still further object of the present invention is to provide methods for using the novel imidazolium cations and their salts produced by the processes of the instant invention. These methods include a variety of applications, both industrial and medical, which result from the properties of the aforesaid imidazolium compounds.

It is thus a further object of the present invention to provide methods of using the compounds of the instant invention as fluorescent dyes for textiles, and for the incorporation into polymer matrices so as to enable their use in as pigments for waterborne paints, films and articles made of polyolefins, e.g. polyethylene or polypropylene.

It is a further object of the present invention to provide compounds useful in the preparation of non-linear optical devices.

Still further, it is an object of the present invention to utilize the compounds of the instant invention for printing fiber materials, for example, polyester, cotton or polyester/cotton blend fabrics.

Another object of the present invention is to utilize the compounds of the present invention as fluorescent tags for biomolecules, so as to enable the labeling of such molecules and the monitoring of the disposition of such molecules by the mammalian body.

A still further object of the present invention involves the use of the compounds of the present invention as components of kits for use in assaying biomolecules tagged with the aforesaid compounds.

Another object of the present invention is to use the process of the invention in combinatorial drug invention systems for labeling and for therapeutic investigation. The instant invention can be used as a linear strategy for combinatorial synthesis.

SUMMARY OF THE INVENTION

The present invention relates to novel imidazolium cations and to processes for their preparation. More particularly, this invention concerns compounds of the formula I

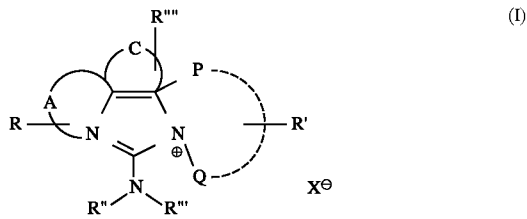

wherein A is a heteroaromatic ring, which may be optionally substituted by one or more R substituents selected from the group consisting of aryl, heteroaryl, lower alkyl, hydroxy, halo, lower alkylamino, amino, nitro, or carboxy substituents;

wherein P or Q are optional substituents, each independently a substituent selected from the group consisting of aryl, heteroaryl, lower alkyl, hydroxy, halo, lower alkylamino, amino, nitro, or carboxy, or P and Q together are a heteroaromatic ring, said P and Q substituents independently or together which may optionally be substituted by one or more R' substituents selected from the group consisting of aryl, heteroaryl, lower alkyl, hydroxy, halo, lower alkylamino, amino, nitro, or carboxy substituents;

C is an optional substituent which is an aromatic or heteroaromatic ring, which may optionally be substituted by one or more R"" substituents selected from the group consisting of aryl, heteroaryl, lower alkyl, hydroxy, halo, lower alkylamino, amino, nitro, or carboxy substituents; R" is hydrogen, a lower alkyl or aryl group, or together with R'" and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group; R'" is a lower alkyl or aryl group, or together with R" and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group; and X is an anion.

The process of the instant invention involves the reaction of a compound of formula II with an N,N-disubstituted-formamide of formula III in the presence of a halogenating agent.

BRIEF DESCRIPTION OF THE DRAWINGS

FIGS. 1A-1 to 1Q-1 show the respective compounds corresponding to FIGS. 1A-1Q.

DETAILED DESCRIPTION OF THE INVENTION

Figure 1A:
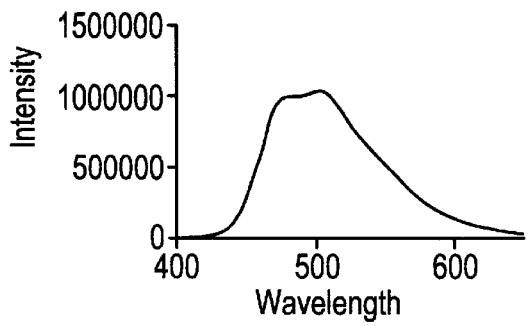
FIGS. 1A–1C are graphs showing the fluorescence spectra of the compounds of the instant invention at an excitation wavelength of 350 nm, acetonitrile solution at room temperature
Figures 1, 1A:
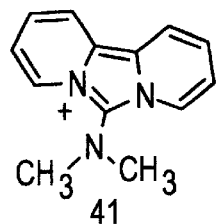
Figure 1B:
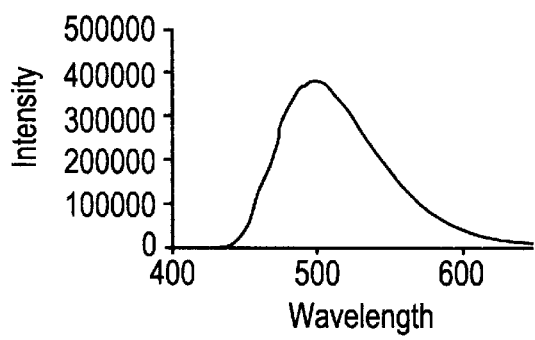
Figures 1, 1B:
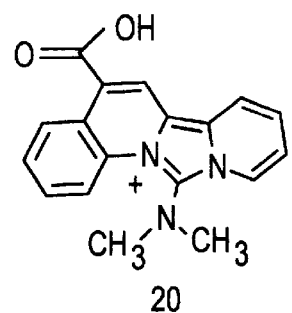
Figure 1C:
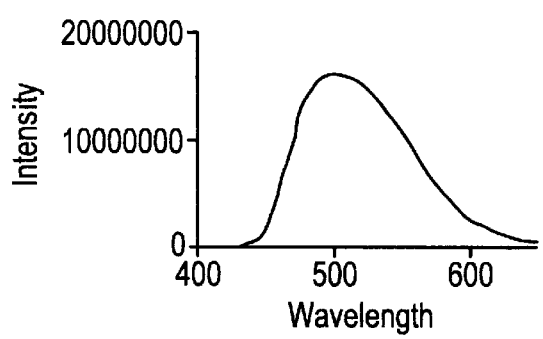
Figures 1, 1C:
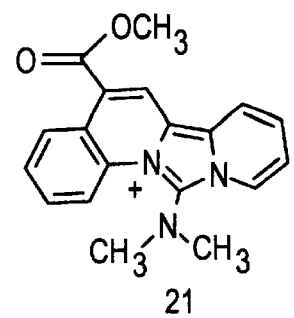
Figure 1D:
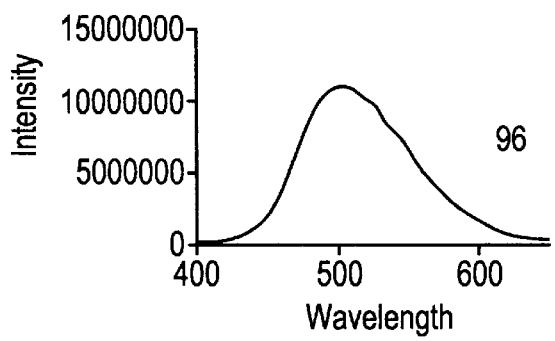
Figure 1E:
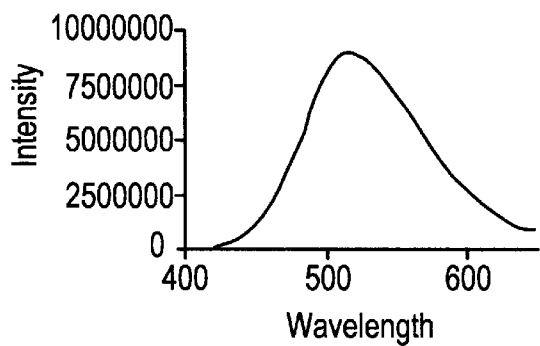
Figures 1, 1E:
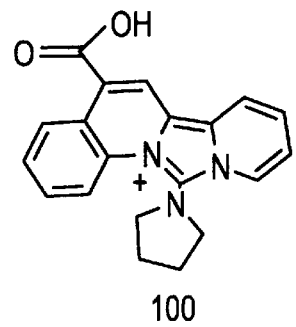
Figure 1F:
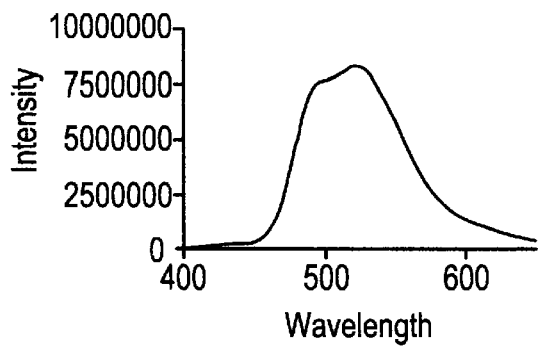
Figures 1, 1F:
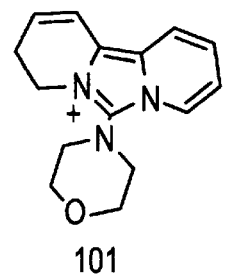
Figure 1G:
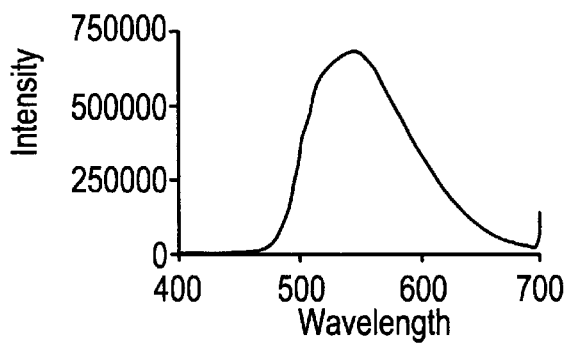
Figures 1, 1G:
Figure 1H:
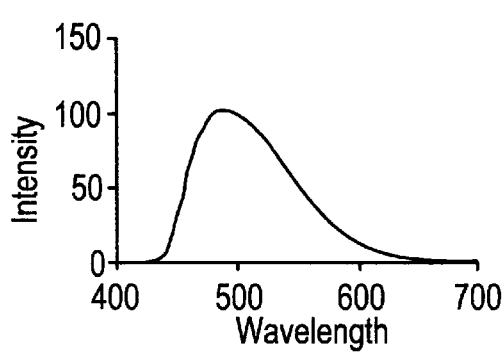
Figures 1, 1H:
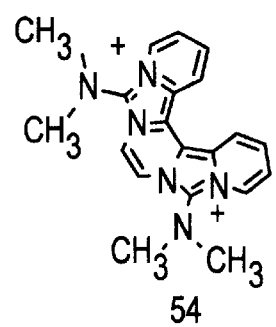
Figure 1:
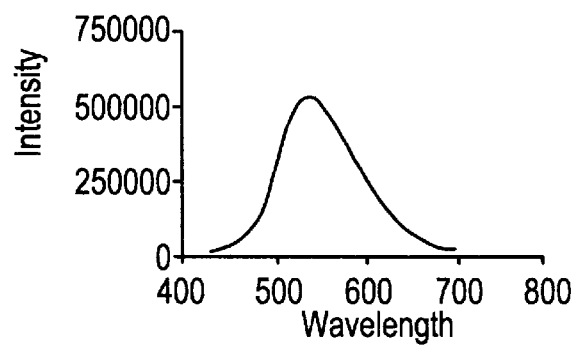
Figure 1:
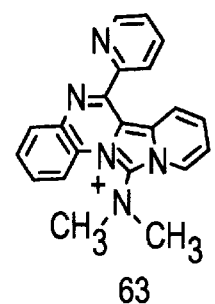
Figure 1J:
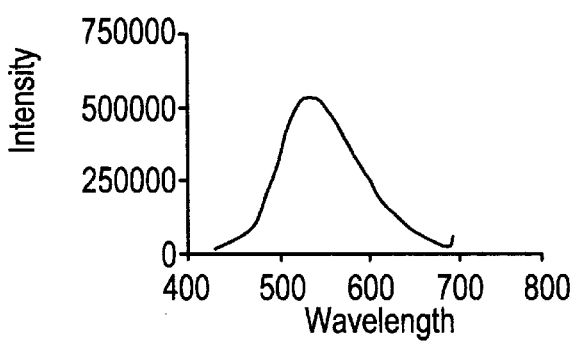
Figures 1, 1J:
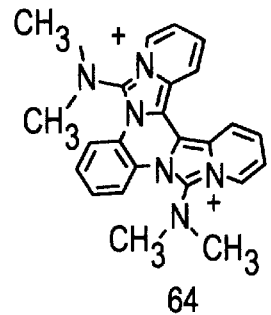
Figure 1K:
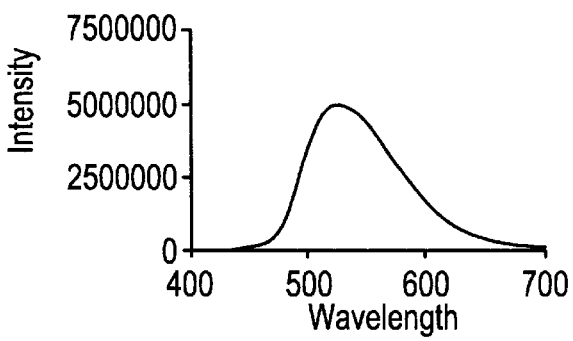
Figures 1, 1K:
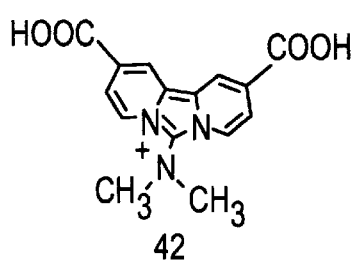
Figure 1L:
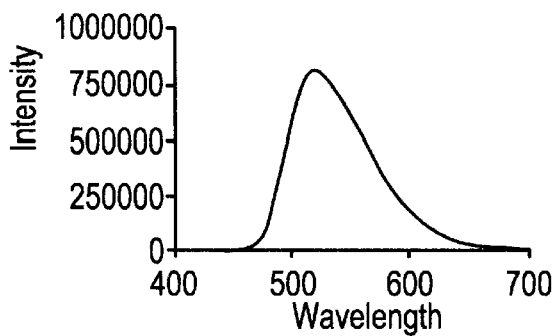
Figures 1, 1L:
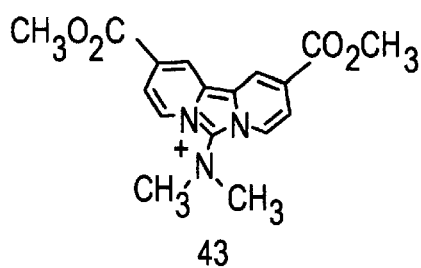
Figure 1M:
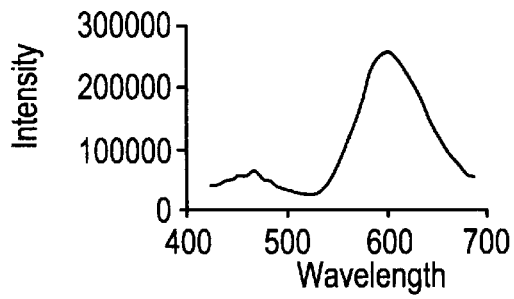
Figures 1, 1M:
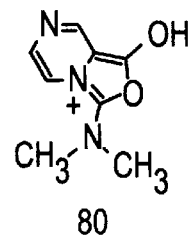
Figure 1N:
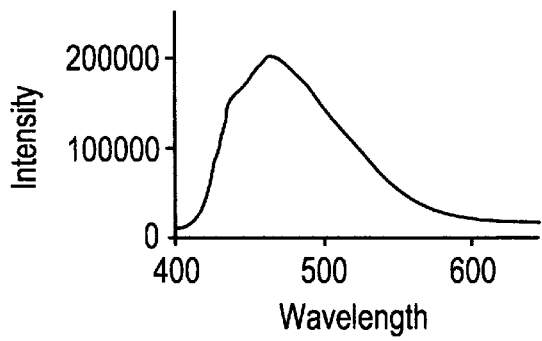
Figures 1, 1N:
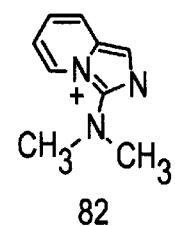
Figure 1O:
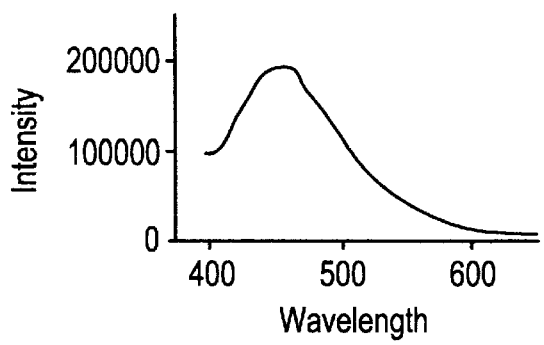
Figures 1, 1O:
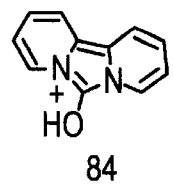
Figure 1P:
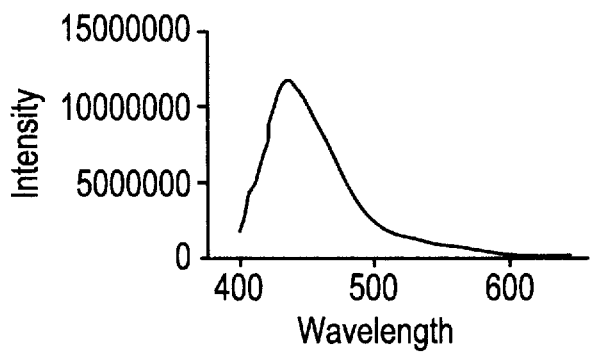
Figures 1, 1P:
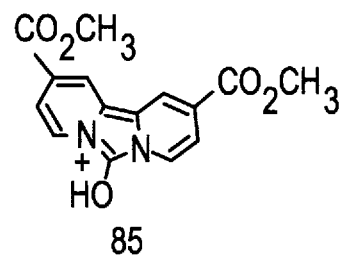
Figure 1Q:
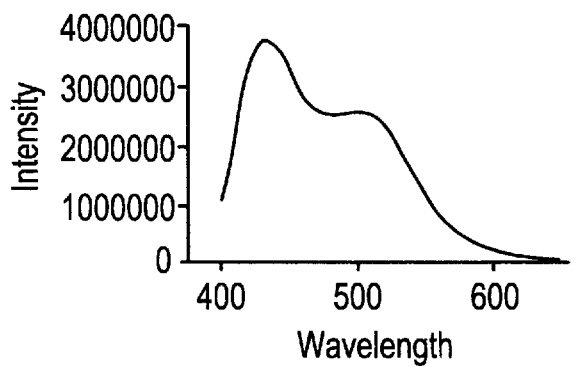
Figures 1, 1Q:
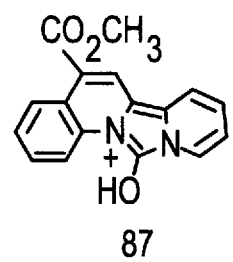
Figure 2A:
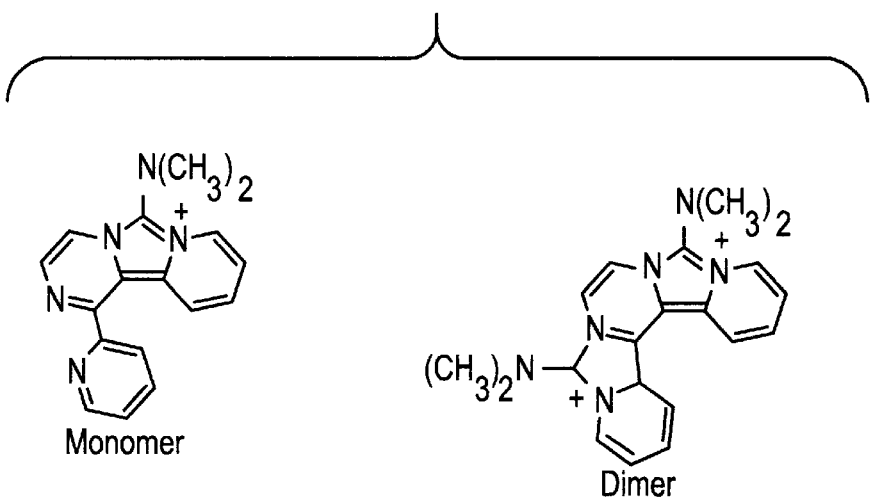
FIG. 2A depicts the structures.
Figure 2B:
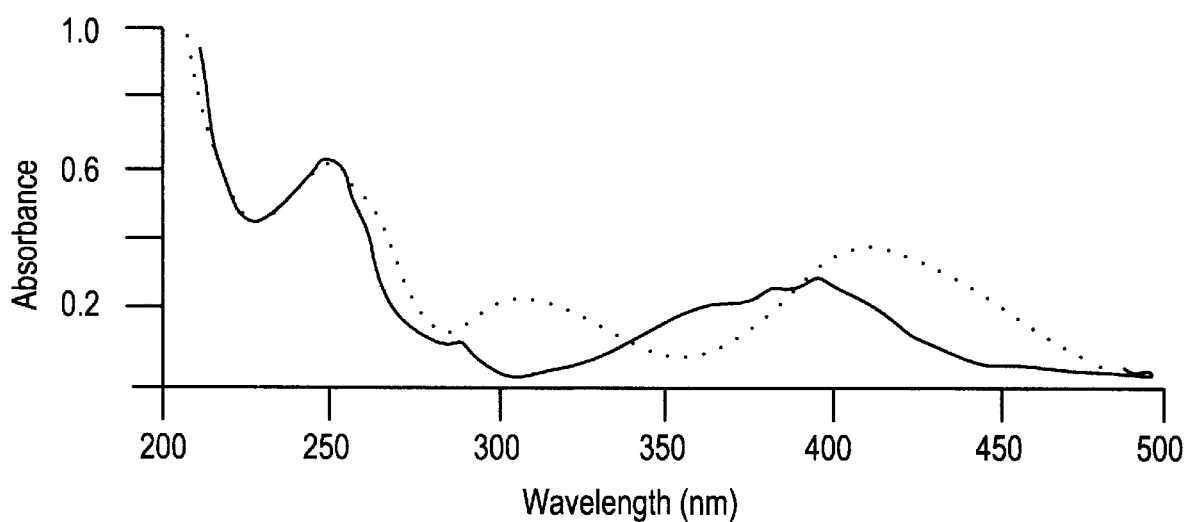
FIG. 2B is a graph comparing the absorbance of Dpp monomer and dimer at 200–500 nm excitation in acetonitrile.
Figure 3A:
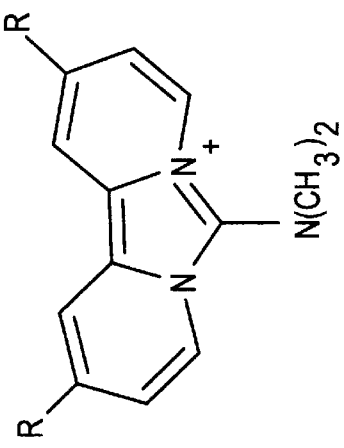
FIG. 3A depicts the general structure and FIG. 3B is a graph showing the fluorescent spectra of 4,4'-disubstituted imidazolium cations having various substituents at 200–500 nm excitation, in acetonitrile.
Figure 3B:
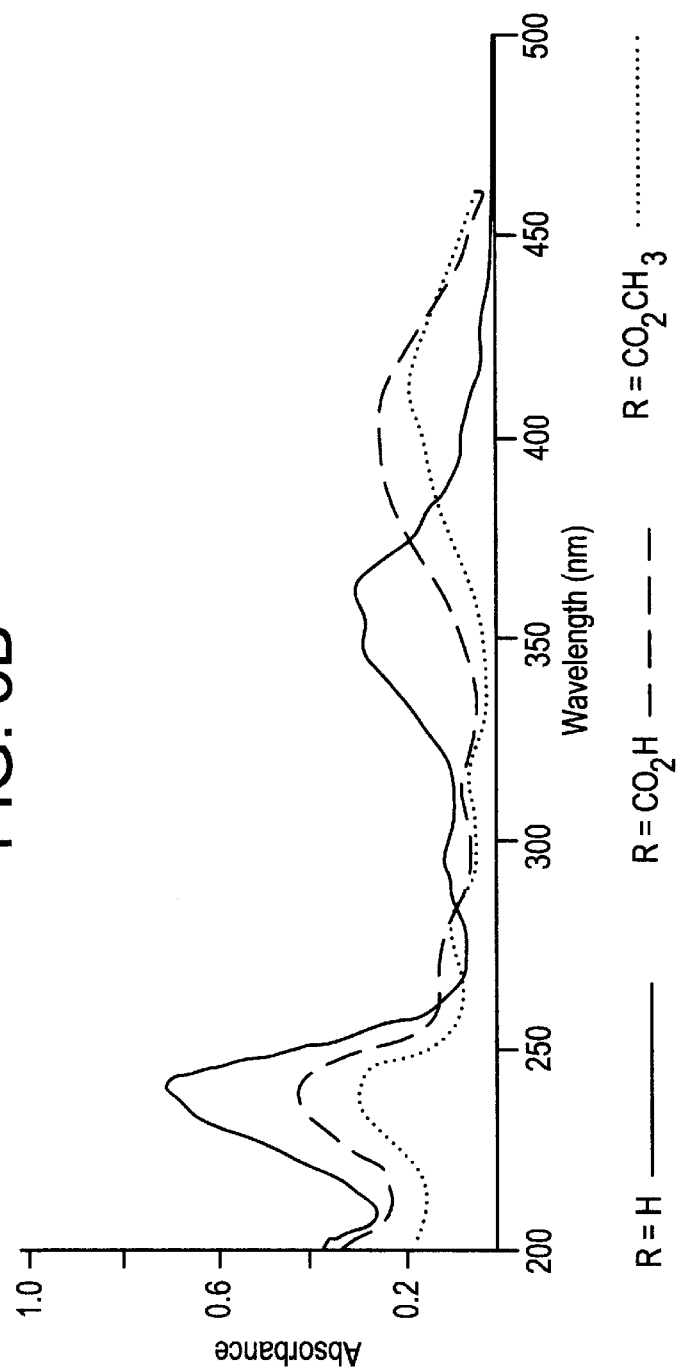

The lower alkyl groups referred to herein preferably contain 1–6 carbon atoms and include methyl, ethyl, propyl, butyl, pentyl, hexyl, and the corresponding branched-chain isomers thereof. These groups are optionally substituted by one or more halo, hydroxy, amino or lower alkylamino groups.

In the instance where R" and R'", together with the nitrogen atom to which they are attached, form a heterocyclic ring having from 5 to 7 members, which may optionally contain a sulfur, oxygen, silicon, selenium or additional nitrogen atom, such heterocyclic rings are typified by pyrrolyl, imidazolyl, pyrazolyl, pyrrolidinyl, imidazolidinyl, piperdinyl, morpholinyl and piperazinyl groups, which can optionally be substituted by lower alkyl groups. Especially preferred for use in the present invention are pyrrolodine, morpholino and piperazinyl groups.

Where the possibility exists for substitution of a phenyl or aryl ring, the position of the substituents may be ortho, meta, or para to the point of attachment of the phenyl or aryl ring to the nitrogen of the hydrazine group. Preferably, the substituents are para or meta to the point of attachment, and where more than one is present on the same ring, they are preferably in the para and meta positions.

The halo atoms in the above formula may be fluoro, chloro, bromo or iodo. The lower alkoxy groups contain 1–6, and preferably 1–3, carbon atoms and are illustrated by methoxy, ethoxy, n-propoxy, isopropoxy and the like.

The A, C, P and Q atomic groups of the compounds of formula I can be selected from a variety of such groups known in the chemical arts. In a preferred embodiment of the present invention, the A and the combination of the P and Q group are each a pyridyl ring. Other embodiments are those wherein the A group is a quinolinyl, piperazinyl, or an anthracenyl group, optionally substituted with R, and R' substitutents.

The compounds of this invention are salts wherein the X- anion is derived from an acid, typically one which is biologically and pharmaceutically acceptable. The resultant salts can thus be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic, methanesulfonic and related acids.

Of the compounds encompassed by formula I, certain substituents are preferred. For instance, the compounds wherein both the A and the combination of the P and Q group are a pyridyl ring are preferred, as are the compounds wherein the A group is derived from a quinolinyl group and the combination of the P and Q group is derived from a pyridyl group. These compounds are the result of the reaction of the N,N-disubstituted-formamide with the appropriately substituted 2,2'-bipyridine or 2-(2-pyridyl)-4-carboxyquinoline. Also highly preferred due to their utility in biomolecular synthesis and various diagnostic applications are the compounds which are the reaction product of an N,N-disubstituted-formamide with an amino acid which has been coupled to 2-(2-pyridyl)-4-carboxyquinoline.

Representative compounds of the present invention include:
12-(dimethylamino-5-carboxy)-pyrido[1',2':3,4]imidazo[1,5-a]quinolin-11-ium perchlorate;
12-(dimethylamino-5-methoxycarbonyl)-pyrido[1',2':3,4] imidazo[1,5-a]quinolin-11-ium perchlorate; 12-(dimethylamino-5-methoxycarbonyl)-pyrido[1',2':3,4] imidazo[1,5-a]quinolin-11-ium perchlorate;
12-(diethylamino-5-carboxy)-pyrido[1',2':3,4]imidazo[1,5-a]quinolin-11-ium perchlorate;
6-(dimethylamino)-dipyrido[1,2-c:2',1'-e]imidazol-5-ium perchlorate;
6-(dimethylamino)-2,10-bis(carboxy)-dipyrido[1,2-c:2',1'-e]imidazol-5-ium perchlorate;
6-(dimethylamino)-2,10-bis(methylcarbonyl)-dipyrido[1,2-c:2',1'-e]imidazol-5-ium perchlorate;
6-(dimethylamino)-6-(2-pyridinyl)-pyrrido[1',2',:3,4] imidazo [1,5-a]pyrazin-5-ium perchlorate;
6-11-bis(dimethylamino)-bis-pyrido[1',2':3,4]imidazo[1,5-a:5',1'-c]pyrazine-5,10-diium diperchlorate;
12-(dimethylamino)-6-(2-pyridnyl)-pyrido[1',2':3,4] imidazo[1,5-a]quinoxalin-11-ium perchlorate;
6,13-bis-(dimethylamino)-bispyrido[1',2':3,4]imidazo[1,5-a:5',1'-c]quinoxaline-5,12-diium diperchlorate;
12-(dimethylamino)-6-(2-pyridinyl)-pyrido[1',2':3,4] imidazo[1,5-a]anthacen-11-ium perchlorate; and
6,13-bis(dimethylamino)-bispyrido[1',2':3,4]imidazo[1,5-a:5',1'-c]anthacen-5,10-diium diperchlorate.

Other especially preferred compounds are the derivatized amino acids:
5-(L-glycyl)-12-dimethylamino-pyridyl[1',2':3,4]imidazo[1,5-a]quinolin-11-ium perchlorate;
5-(L-glycylmethylester)-12-dimethylamino-pyridyl[1',2':3,4]imidazo[1,5-a]quinolin-11-ium-perchlorate;
5-(L-leucinyl)-12-dimethylamino-pyridyl[1',2':3,4]imidazo[1,5-a]quinolin-11-ium-perchlorate;
5-(L-leucinemethyl ester)-12-dimethylamino-pyridyl[1',2':3,4]imidazo[1,5-a]quinolin-11-ium-perchlorate;
5-(L-histidInyl)-12-dimethylamino-pyridyl[1',2':3,4] imidazo[1,5-a]quinolin-11-ium-perchlorate.
(L-histidinylmethyl ester)-12-dimethylamino-pyridyl[1',2':3,4]imidazo[1,5-a]quinolin-11-ium-perchlorate;
5-(L-glycylglycyl)-12-dimethylamino-pyridyl[1',2':3,4] imidazo[1,5-a]quinolin-11-ium-perchlorate;
5-(L-glutamyl)-12-dimethylamino-pyridyl[1',2':3,4]imidazo[1,5-a]quinolin-11-ium-perchlorate.

Many suitable starting materials for the compounds of the instant invention are generally known in the art. For instance, Balzani et al., *Chemical Reviews,* 1996, Vol. 96, No. 2, pp. 759–832 and Juris et al., *Coordination Chem. Reviews,* 1988, Vol. 84, pp 85–277, contain details of the preparation of numerous compounds which can be utilized as starting materials for the processes of the instant invention due to their inclusion of the N—C—C—N moiety. Many suitable compounds are also commercially available, for instance, from Aldrich Chemical Co.

Some particularly suitable starting materials for use in the practice of the instant invention are the following known compounds:
2,2'-bipyridine;
4-chloro-2,2'-bipyridine;
4-bromo-2,2'-bipyridine;
4-amino-2,2'-bipyridine;
4-dimethylamino-2,2'-bipyridine;
4-methoxy-2,2'-bipyridine;
4-nitro-2,2'-bipyridine;
4-benzyl-oxy-2,2'-bipyridine;
4-(triethylphophonio)-2,2'-bipyridine;
6-methyl-2,2'-bipyridine;
6-p-styryl-2,2'-bipyridine;
6-p-tolyl-2,2'-bipyridine;
3,3'-dimethyl-2,2'-bipyridine;
2cyanopyridine;
3,3-dicarboxyisopropyl-2,2'-bipyridine;
4,4'-dimethyl-2,2'-bipyridine;
4,4'-dichloro-2,2'-bipyridine;
4,4'-dibromo-2,2'-bipyridine;
4,4'-dinitro-2,2'-bipyridine;
4,4'-diamino-2,2'-bipyridine;

4,4'-disulphonate-2,2'-bipyridine;
4,4'-bis(diethylamino)-2,2'-bipyridine;
4,4'-diethoxy-2,2'-bipyridine;
4,4'-diphenoxy-2,2'-bipyridine;
4,4'-dibenzyloxy-2,2'-bipyridine;
4,4'-diphenyl-2,2'-bipyridine;
4,4'-dibezyl-2,2'-bipyridine;
4,4'-distyryl-2,2'-bipyridine;
4,4'-dicarboxy-2,2'-bipyridine;
4,4'-di-tert-butyl-2,2'-bipyridine;
4,4'-dinonadecyl-2,2'-bipyridine;
4,4'-distearyl-2,2'-bipyridine;
4,4'-dicarboxymethyl-2,2'-bipyridine;
N,N'-di(dodecyl)-2,2'-bipyridine-4,4'-dicarboxyamide;
N,N'-di(hexadecyl)-2,2'-bipyridine-4,4'-dicarboxyamide;
4,4'-dicarboxyethyl-2,2'-bipyridine;
4,4'-dicarboxyisopyl-2,2'-bipyridine;
4,4'-dicarboxycyclohexyl-2,2'-bipyridine;
4,4'-dicarboxybenzyl-2,2'-bipyridine;
4,4'-dicarboxynapth-2-yl-2,2'-bipyridine;
4,4'-dicarboxynaphthan-1-yl-2,2'-bipyridine;
4,4'-dicarboxydihydrocholesteryl-2,2'-bipyridine;
N,N'-di(ethyl)-2,2'-bipyridine-4,4'-dicarboxamide;
4-carboxy-4'-methyl-2,2'bipyridine;
4-vinyl-4'-methyl-2,2'-bipyridine;
5,5'-dimethyl-2,2'-bipyridine;
5,5'-dicarboxyethyl-2,2'-bipyridine;
5,5'-bisacetoamido-2,2'-bipyridine;
5,5'-dicarboxyisopropyl-2,2'-bipyridine;
6,6'-dimethyl-2,2'-bipyridine;
4,4',5,5'-tetramethyl-2,2'-bipyridine;
2,2'-bipyrazine;
protonated 2,2'-bipyrazine;
2,2'-bipyrimidine;
4,4'-dimethyl-2,2'-bipyrimidine;
6,6'-dimethyl-4,4'-bipyrimidine;
3,3'-bipyridazine;
4-methyl-2(2'-pyridyl)-pyrimidine;
6-methyl-4-(2'-pyridyl)-pyrimidine;
2-(2-aminoethyl)pyridine;
o-phenanthroline-5,6-diimine;
pyridyl-2-imine;
2-(2-pyridyl)imidazolate anion;
2-(2-pyridyl)imidazole;
2,2'-biimidazote dianion;
2,2'-diimidazote anion;
2,2'-biimidazole;
2,2'-dibenzimidazolate dianion;
2,2'-dibenzimidazolate anion;
2,2'-dibenzimidazole;
1-(2-pyridyl)-3,5-dimethyl-pyrazole;
2-(2'-thiazolyl)-pyridine;
2-(2'-pyridyl)-4-methyl-thiazole;
4,4'-bithiazole;
2,2'-bi-2-thiazoline;
2-p-tolyl-pryidinecarboxaldimine;
2,2'-biquinoline;
4,4'-dimethyl-2,2'-bipyridine;
2,3-bis(2-pyridyl)-(pyrazine);
2,3-di-2-pyridylquinoxaaline;
2,3,7,8-tetra-2-pyridylpyrazino[2,3-g]quinoxaline;
2,2',3,3'-tetra-2-pyridyl-6,6'-biquinoxaline;
1,2-bis[4-(4'-methyl-2,2'-bipyridinyl)]ethane;
1,5-bis[4-(4'-methyl-2,2'-bipyridinyl)]petane;
1,4-bis[4-(α-ethyl)-4'-methyl-2,2'-bipyridyl]benzene;
1,12-bis[4,(4'-methyl-2,2'-bipyridyl)dodecane;
2,2',2"-tripyridine;
4'-phenyl-2,2',2"-tripyridine;
4,4',4"-triphenyl-2,2',2"-tripyridine;
2,4,6-tripyridyl-s-triazine;
4-ethynyl-2,2'-bipyridine;
1,12-bis(4-methyl-2,2'-bipyrid-4'-yl)-2-11-diazadodecane;
1,11-bis(4-methyl-2,2'-bipyrid-4'-yl)-6-methyl-2,6,10-triazaundecane trans-1,2-bis(4'-methyl-2,2'-bipyrid-4-yl)-ethene;
1,4-bis(4-methyl-2,2'-bipyridin-4'-yl)buta-1,3-diene;
1,4-bis(4-methyl-2,2'-bipyridin-4'-yl)buta-1,3-diene;
1,4-bis[2-(2,2'-bipyridin-5-yl)ethenyl]-bicyclo[2.2.2]octane;
1,4-bis(4-methyl-2,2'-bipyridin-4'-yl)-2-cyclohexene-5,6-dicarboxylic acid diethyl ester;
10-bis[[[(2,2'-bipyridinyl-5-yl)carbonyl]-enzylamino]methyl]anthracene;
1,3,5-tris[[[(2,2'-bipyridyl-5-yl)carbonyl]-benzylamino]methyl]benzene;
1,3,5-tris[[[5-(ethoxycarbonyl-(2,2'-bipyridyl-5-yl)carbonyl)benzylamino]methyl]phenyl]benzene;
1,3,5-tris[4-[[(2,2'-bipyridyl-5-ylcarbonyl)benzylamino]methyl]phenyl]benzene;
2,2':6,2":6",2"'-quaterpyridine;
2,2':4',4":2",2"'-quaterpyridine;
1,2-bis(6'-methyl-2,2'-bipyridin-6-yl)-ethane;
1,4,7,10,13,16-hexakis[(2,2'-bipyridin-6-yl)methyl]-1,4,7,10,13,16-hexaazacyclooctodecane;
2,2':3',2":6",2"'-quaterpyridine;
2,3-bis(2-pyridyl)pyrazine;
2,5-bis(2-pyridyl)pyrazine;
2,3-bis(2'-pyridyl)quinoxaline;
6,7-dimethyl-2,3-bis(2-pyridyl)quinoxaline;
6,7-dichloro-2,3-bis(2-pyridyl)quinoxaline;
2,3-bis(2'-pyridyl)benzo[g]quinoxaline;
2,2',3,3'-tetra-2-pyridyl-6,6'-biquinoxaline;
2-pyridylacetonitrile;
2,2'-biquinoline;
2,2'-biquinoline-4,4'-dicarboxylic acid;
2,2'-biquinoline-4,4'-dicarboxylic acid dipotassium salt trihydrate;
2,2'-biquinoline-4,4'-dicarboxylic acid disodium salt dihydrate;
2,4-bis(5,6-diphenyl-1,2,4-triazin-3-yl)pyridine;
3-(2-pyridyl)-5,6-di(2furyl)-1,2,4-triazine-5',5"-disulfonic acid disodium salt;
3-(2-pyridyl)-5,6-diphenyl-1,2,4-triazine;
3-(2-pyridyl)-5,6-diphenyl-1,2,4-triazine-4'-4"-disulfonic acid monosodium salt;
2,4,6-tri(2-pyridyl)-s-triazine;
2,3-diaminopyridine;
1,2-dicyanobenzene;
1,2,4,5-tetracyanobenzene; and
S(−)-1-formyl-2-(methoxymethyl)pyrrolidine In certain cases, the preparation of the compounds of the instant invention involves the preparation and use of novel starting materials. A general scheme for the preparation of several of such starting materials is shown below as Scheme I. In this scheme, the preparation of several necessary starting materials for the process of the instant invention are the novel compounds of formula I wherein A represents the atomic group necessary to form a quinoline ring, and B represents the atomic group necessary to form a pyridyl ring is shown, using the known starting materials isatin and 2-acetylpyridine. In step A, isatin and 2-acetylpyridine are reacted in the presence of a strong base, such as sodium or potassium hydroxide to form the sodium or potassium salt of 2-(2-pyridyl)-4-carboxyquinoline. This salt can then be converted to the free acid by treatment with a dilute solution of a strong mineral acid, such as hydrochloric or sulfuric acid. Treatment of the free acid with the appropriate alkanol and a strong acid affords the alkyl ester of the acid. This alkyl ester can then be reduced, using, for instance, sodium borohydride or another reducing agent to give the corresponding alcohol. Alternatively, the free acid can be converted to the corresponding acyl halide by treatment with thionyl chloride with or without the presence of a non-polar hydrocarbon solvent. As can be expected the acyl halide can serve as a starting material to produce additional compounds, such as the ethylene glycol ester, as well as the corresponding amide compounds such as by reaction with a diamine. These compounds have a reactive termini that can be used to generate additional novel compounds for use with the instant invention.

In a similar fashion, the pyrazine analogs of the compounds in Scheme I can be prepared by substituting 2-acetylpyrazine for 2-acetylpyridine. For example, 2-(2-pyrazinyl)-4-carboxyquinoline, (4)2-(2-pyrazinyl)-4-carboxymethylquinoline, (5)2-(2-pyrazinyl)-4-hydroxymethylquinoline, (6)2-(2-pyrazinyl)-4-carboxyquinoline acid chloride; (7)2-(2-pyrazinyl)-4-carboxyquinoline ethylene glycol ester; and 2-(2-pyrazinyl)-4-carboxyquinoline, methyl benzyl ester, can be prepared by use of the appropriate 2-acetylpyrazine starting material.

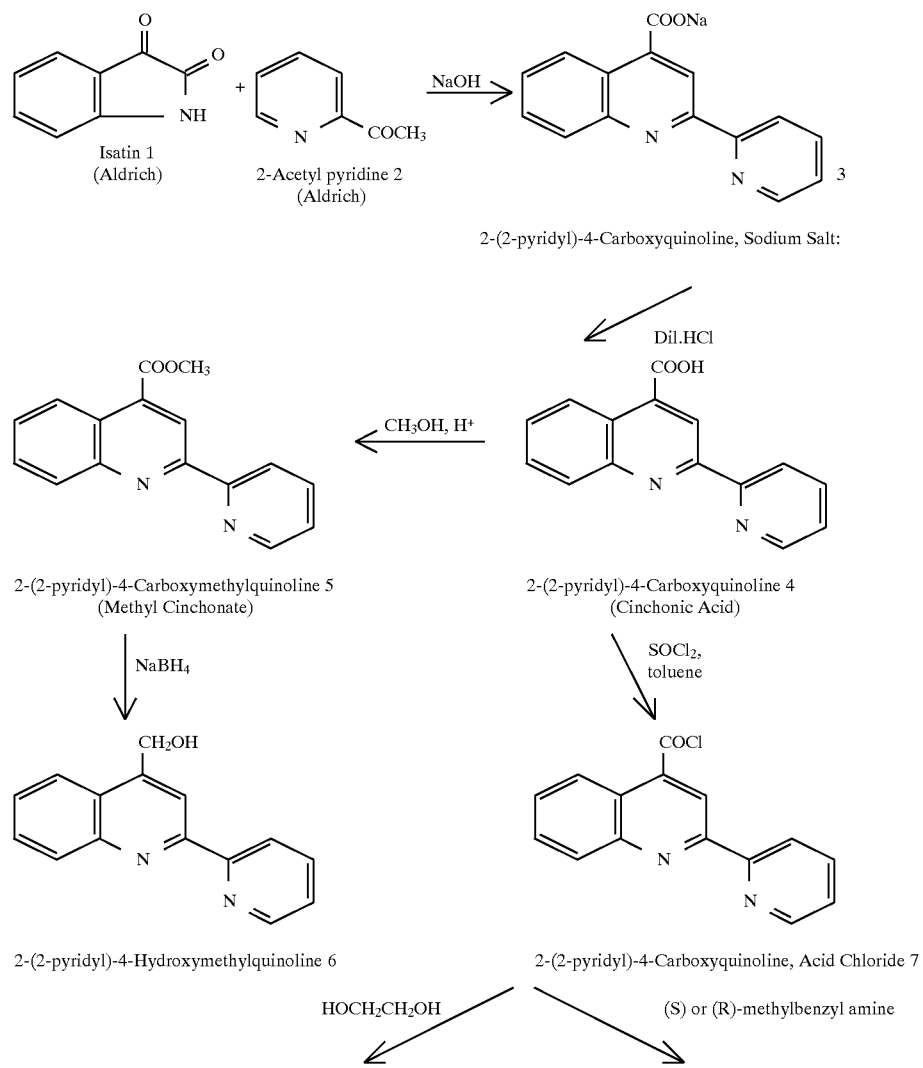

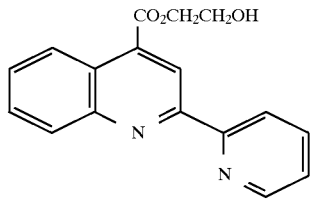

2-(2-pyridyl)-4-Carboxyquinoline,
Ethylene glycol ester 8

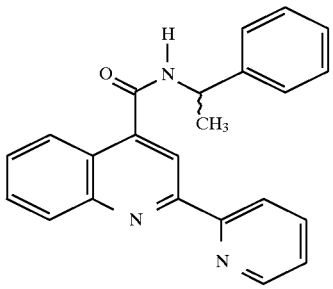

(S) or (R)-2-(2-pyridyl)-4-Carboxyquinoline,
methylbenzyl amide 9

A particularly useful embodiment of the present invention involves the reaction of acyl halide compounds with a natural or synthetic amino acid. As shown in Scheme II below, this reaction results in a starting material which links the amino acid to the carbonyl moiety. Generally, this reaction is conducted in an anhydrous polar solvent, such as anhydrous acetonitrile, in the presence of an acid acceptor, such as triethylamine. Preferred for use in this reaction are the naturally and non-naturally occurring amino acids and their alkyl, especially methyl, or benzyl esters. The reaction can also be extended to include peptides of two or more amino acids, and the alkyl or benzyl esters of amino acids and can thus function as a method of synthetically preparing a "tag" or label of such a peptide. Since non-natural amino acids and peptides can be derived from β-lactams fluorescent β-lactams, can be generated by the instant methodology. Particularly useful are fluorinated amino acids and β-lactams.

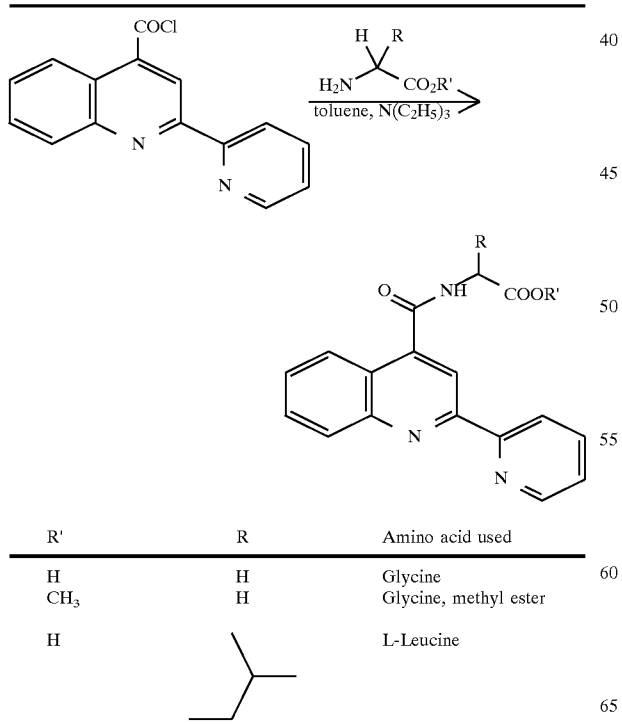

| R' | R | Amino acid used |
|---|---|---|
| H | H | Glycine |
| CH$_3$ | H | Glycine, methyl ester |
| H | ![isobutyl] | L-Leucine |
| CH$_3$ | ![isobutyl] | L-Leucine, methyl ester |
| H | ![imidazolylmethyl] | L-Histidine |
| CH$_3$ | ![imidazolylmethyl] | L-Histidine, methyl ester |
| H | ![glycylamide] | Gly—Gly |
| H | ![CH2CO2H] | Aspartic Acid |
| H | ![CH2CH2CO2H] | Glutamic acid |

The novel process of the instant invention involves the reaction of a starting material of the general formula

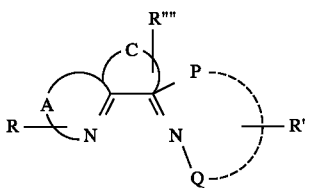 (II)

wherein A, C, P, R, R' and R"" are as hereinbefore defined, with an N-substituted or N,N-disubstituted formamide of the formula

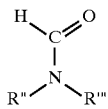 (III)

wherein R" and R'" are as herein before defined, in stoichiometric amounts, in the presence of a halogenating agent.

Suitable halogenating agents are those such as thionyl chloride ($SOCl_2$), thionyl bromide ($SOBr_2$), phosphorus oxychloride ($POCl_3$), phosphorus tribromide ($PBr_3$), phosphorus triiodide ($PI_3$), phosgene ($COCl_2$), phosphorus thiochloride ($PSCl_3$), thiophosgene ($CSCl_2$), oxalyl chloride (ClCOCOCl), oxalyl bromide (BrCOCOBr), phosphorous pentachloride ($PCl_5$) and phosphorus trichloride ($PCl_3$). Of these, phosphorus oxychloride ($POCl_3$), oxalyl chloride (ClCOCOCl), and thionyl chloride ($SOCl_2$) are highly preferred.

Depending upon the nature of the reactants, a solvent can be used or the reaction can proceed neat. When a solvent is utilized, it is typically a nonpolar aprotic solvent, such as benzene, toluene, hexane, etc. but polar solvents such as acetonitrile can also be used.

Reaction conditions for the instant process vary depending upon the nature of the starting materials, and the presence or absence of a solvent. Typical temperatures range from 0° C. to room temperature. With highly reactive starting materials, a somewhat lower temperature may be desirable, as well as the use of an inert atmosphere, such as a nitrogen or argon atmosphere, to inhibit side reactions.

Anhydrous conditions will also help to minimize possible side reactions, especially where more than one set of reactive nitrogen atoms are available. Where the various R, R'" and R"" substitutents would allow side reactions, they can be suitably protected, prior to the conduct of the reaction, to avoid such reactions. Typical protecting groups useful for such procedures are well-known in the art, and can be removed after isolation of the imidazolium compound.

Where the structure of the starting materials contains more than one N—C—C—N moiety, it will be appreciated that both reactive sites can be the subject of the instant process by use of two equivalents of the disubstituted formamide reactant. Numerous "monomer" (containing a single imidazolium ring) and "dimer" (containing two imidazolium rings) compounds of this type can be produced by the judicious choice of starting materials.

The process of the instant invention provides a convenient and facile process for use in combinatorial synthesis, especially as described by Armstrong et al., *Acc. Chem. Res.*, 1966, 29. pp. 123–131, Ellman, *Acc. Chem. Res.*, 1996, 29 pp. 132–143, and Gordon et al., *Acc. Chem. Res.*, 1996, 29, pp. 144–154.

The compounds of the instant invention possess valuable properties which make them useful in numerous commercial applications, both industrial, medical and therapeutic.

The compounds of the instant invention possess interesting spectroscopic properties, especially fluorescent properties, which enable their use in a variety of commercial applications. For instance, the compounds can be used as fluorescent dyes in a range of blue, red, green, yellow colors, and especially blue and green colors. The color of fluorescence may be different from the absorption color. They can be utilized directly for the dyeing of textiles, and/or may be incorporated into commercially available polymer matrices, in typically, but not limited to, an amount of about 1–3% by weight, based upon the polymer matrix. Preferred apolar polymer matrices are selected from the group consisting of polymethyl methacrylate, polystyrene, polybutadiene-modified polystyrene, polycarbonate, polyvinyl chloride and polyamide, with polymethyl methacrylate and polystyrene matrices being particularly preferred. Other polymer matrices which can also be used include polycondensates based upon urea and formaldehyde or polyamide.

The fluorescent pigments are prepared in a conventional manner, such as is illustrated in U.S. Pat. No. 5,470,502, whose teachings are herein incorporated by reference. Generally, the fluorescent compound of the instant invention is incorporated into the polymer matrix by extrusion or injection molding. The process of incorporation generally operates at a temperature range of about 150° C. to about 250° C., depending upon the polymer matrix utilized. When polymethyl methacrylate is used, the temperature is generally at a range of about 200° C. to about 240° C.

The novel fluorescent pigments formed by mixing the compounds of the present invention with a polymer matrix are highly suitable for pigmenting waterborne paints and films and articles made of polyolefins, e.g. polyethylene or polypropylene, and for printing fiber materials, for example, fabrics in polyester or cotton or polyester/cotton blends.

Such fluorescent pigments possess high luminenscence and advantageous application properties, for example, high lightfastness and a low migration tendency.

The possession of fluorescent properties further enables the use of the compounds of the instant invention in a variety of medical, pharmaceutical and diagnostic applications. Fluorescent clonal markers can be utilized to elucidate various biological mechanisms, in both animal and plants such as the embryogenesis of an organism, drug binding sites, and drug disposition in the body.

For instance, by attaching a fluorescent compound of the instant invention to a biomolecule such as the end of one arm of a probe sequence of nucleic acids, and a non-fluorescent quench moiety to the end of the other arm of a probe sequence of nucleic acid, the synthesis of specific nucleic acids can be monitored. Similarly, when such fluorescent compounds are used in nucleic acid amplification assays, gene detection is homogeneous and sensitive. Still further, nucleic acid probes containing the fluorescent compounds of the instant invention can be introduced into living cells, thus enabling the origin, movement, and fate of specific mRNAs to be traced. Such methods of attaching fluorescent compounds to such probes have been described in the art, for example in Tyagi et al., *Nature Biotechnology*, 14, pp. 303–308, and T. Stein *Chem. Eng. News, Jul.* 18, 1994, pp. 34–44. By utilizing the various compounds of the instant invention which emit light of a different wavelength, detection of many different targets in the same solution can be identified. For example, a two-dimensional array of immobilized molecular beacons derived from the compounds of the instant invention can be used in a single assay to carry out an extensive survey of an amplified genomic region. Fluorescence is especially useful to probe proteins, and DNA.

In similar fashion, the compounds of the instant invention can be utilized as fluorescent tags for any variety of biomolecules to enable the tracking and the disposition of such molecules. Especially important biomolecules which can be tagged by the instant compounds include amino acids, peptides, proteins, β-lactams, oligonucleotides, RNA, DNA, and lipids. The compounds of the instant invention can thus be included in kits to utilize as labeling agents for such biomolecules in various diagnostic and research applications. Methods for utilizing such fluorescent tags for biomolecules are described in, for instance, Rich et al., *J. Am. Chem. Soc.*, (1995), 117, 733–739, Bakthavalam et al., *J. Med. Chem.*, (1991), 34, 3235–3241, Kraus et al., *Chem. Rev.*, (1996), 96, 523–527, and Wilchek et al., *Analytical Biochemistry*, (1988), 171, 1–32, whose teachings are herein incorporated by reference, especially those pertinent to the development of biotin related-systems.

A further alternative to labeling already formed biomolecules involves the ab initio synthesis of biomolecules using amino acids which have been reacted in accordance with the process of the instant invention to contain the fluorescent tag within their structure. Typically, a solution of the amino acid, ester thereof or a β-lactam in an anhydrous polar solvent, such as acetonitrile, is reacted with a compound of the instant invention which contains an acyl halide functional group, such as, for instance, the acyl chloride of 2-(2-pyridyl)-4-carboxyquinoline, in the presence of an acid acceptor such as triethylamine. This reaction is typically conducted at temperatures of about 0° to about 20° C. Typical reaction times range from about 1 to 10 hours depending upon the exact nature of the reactants. Using this method, one can prepare fluorescent amino acids, both natural and synthetic, which can then be utilized directly in the synthesis of biomolecules to provide fluorescent versions thereof. β-lactams so modified can be used to generate non-naturally occuring amino acids incorporating flourescent characteristics.

Further, the compounds of the instant invention can be used as fluorescent sensors for transition metals due to the advantages of using a fluorescent tag which can be detected at a very low concentration level. Such usage is described, for instance, by Fabbrizzi et al., *Chem. Euro. J.*, (1996), 2, pp. 75 et seq., whose teachings are herein incorporated by reference.

Another utility wherein the instant compounds can be used is in the preparation of non-linear optical polymers. By dissolving a compound of formula I in a polymer, subjecting the polymer to a large electric field at or above its glass transition temperature, and cooling the polymer, there is obtained a material with second-order optical non-linearity as described by Marder et al., *Science*, (1994) 263, pp 1706–1715.

The compounds of the instant invention can also be utilized to label various therapeutic agents to enable their disposition in the body. As such, therapy with such labeled therapeutic agents can be closely monitored with respect to target organs and tissues. This is particularly useful in the treatment of various cancers, especially those of a solid tumor type, where localization of the chemo-therapeutic agent is extremely important, and dosage, due to the possibility of side-effects, must be closely monitored. Similarly, the use of such labeled antibiotics can assist in efficacy determinations of penicillins and antibiotics.

The compounds of the invention additionally exhibit antifungal and antimicrobial activity against *Candida albicans*, as well as antiviral activity (HSV). By virtue of such properties, they can be formulated into pharmaceutical compositions, and used to treat infestations and infections caused by these invasive organisms.

The invention will be further illustrated by the following Examples, which are to be considered illustrative of the invention, and not limited to the precise embodiments shown.

PREPARATION OF STARTING MATERIALS

EXAMPLE A

Preparation of Sodium 2-(2-pyridinyl)-4-carboxyquinoline carboxylate 3

Isatin 1 (8.0 g), and acetylpyridine (6.0 g) 2 are thoroughly mixed in a 250 mL beaker. To this is added, while stirring with a glass stirring rod, 30 g of 33% NaOH, which has been previously cooled to 5° C. Stirring is continued until the contents harden (at this point the temperature is approximately 60° C.). Water (30 mL) is then added, resulting is a fine purple/red slurry (has a metallic sheen). Cooling to 50° C., followed by filtration gives the crude product (3) as a red/purple solid. The solid is washed with ethanol and then acetone, and allowed to dry (10–15 g). Repeated crystallizations from a minimum amount of hot water (decolorizing-carbon which is used to remove the colored impurities) gives 10 g of 2 as a white solid.

$^{13}$C (100 MHz, D$_2$O): δ 116.326(C—H), 123.11 (C—H), 123.987 (C) 125.210 (C—H), 126.110 (C—H), 128.287 (C—H), 128.546 (C—H), 131.115 (C—H), 138.727(C—H), 147.633 (C), 148.171 (C), 149.312 (C—H), 155.072 (C), 156.160 (C), 175.457 (C=O)

EXAMPLE B

Preparation of 2-(2-pyridinyl)-4-quinoline carboxylic acid 4 (trivial name: 2-(2-pyridyl)-cinchoninic acid)

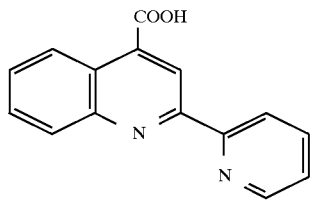

4

The free acid is prepared by neutralizing an aqueous solution of the sodium 2-(2-pyridyl)-4-carboxyquinoline carboxylate 3 with 10% HCl. The acid is somewhat soluble in acidic solution, and care should be taken not to overacidify; a pH of 7 is optimum. The solid is filtered, washed with 40 mL of acetone and allowed to air dry.

EXAMPLE C

Preparation of 4-carboxymethyl-2-(2-pyridyl)-quinoline 5

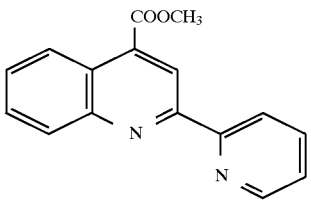

Dry methanol (250 mL) is placed into a 500 mL round bottom flask and cooled to 0°–5° C. in an ice bath. To the stirring methanol is added 10 g of 2-(2-pyrininyl)-4-quinoline carboxylic acid 4, and 20 mL of $H_2SO_4$ (98%). The mixture is then refluxed for 18 hours. The resulting solution is poured over 500 mL of ice water. The solid is filtered (crude 5) and the filtrate is extracted with chloroform (3×200 mL). The extracts are combined, dried over anhydrous sodium sulfate, and the solvent removed under reduced pressure. The solids are combined, and recrystallized from hot toluene (activated carbon), yielding 8.0 g of the title compound 5 as a fluffy white solid. $^1$H NMR (CDCl$_3$, 300 MHz): δ 3.22 (s, 3H), 7.32 (dd, J=7.7, 4.5 Hz, 1H), 7.60 (ddd, J=7.70, 7.70, 1.3 Hz, 1H), 7.72 (ddd, J=8.3, 7.7, 1.3 Hz, 1H), 7.80 (ddd, J=7.7, 7.7, 1.0, 1H), 8.18 (d, J=8.3 Hz, 1H), 8.60 (d, J=7.8 Hz, 1H), 8.78 (d, J=7.8 Hz, 1H), 9.04(s, 1H). $^{13}$C NMR (CDCl$_3$, 300 MHz) δ 52.55 (CH), 120.25 (CH), 121.60 (CH), 124.29 (CH), 125.01 (C), 125.49 (CH), 128.23 (CH), 129.71 (CH), 130.31 (CH), 135.42 (C), 136.93 (CH), 148.73 (CH), 149.10 (CH), 155.32 (C), 155.46 (C), 166.67 (C).

EXAMPLE D

Preparation of 4-hydroxymethyl-(2,2-pyridinyl)-quinoline 6

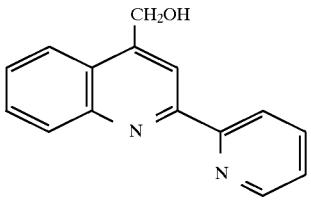

Dry methanol (250 mL) is placed into a 500 mL round bottom flask. To the stirring methanol is added 2.5 g of 4-carboxymethyl-2-(2-pyridyl)-quinoline 5, and 7.0 g of sodium borohydride. The solution is then refluxed for 5 hours. After cooling to room temperature, the reaction mixture is poured into a saturated solution of ammonium sulfate (500 mL), and extracted with chloroform (3×200 mL). The extracts are combined and dried over anhydrous sodium sulfate. Solvents are then removed under reduced pressure using a rotary evaporator. The resulting oil is allowed to solidify, and recrystallized from hot toluene (activated carbon) to yield 1.5 g of the title compound as a colorless solid.

$^1$H NMR (CDCl$_3$, 300 MHz): δ 5.15 (s, 2H, CH$_2$), 7.55 (m, 1H, CH), 7.60 (dd, J=8.2, 8.2 Hz, 1H), 7.80 (dd, J=8.2, 8.2 Hz, 1H), 8.00 (dd, J=8.0, 8.0 Hz), 8.10 (d, J=8.2 Hz, 1H), 8.15 (d, J=8.15 Hz, 1H), 8.62 (d, J=7.0 Hz, 1H), 8.72 (s, 1H), 8.76 (dd, J=6.3, 1 Hz). $^{13}$C NMR (CDCl$_3$, 75 MHz): δ 60.40 (CH2), 115.62 (CH), 121.71 (CH), 123.85 (CH), 125.12 (CH), 125.93 (C), 127.33 (CH), 130.04 (CH), 130.10 (CH), 137.95 (CH), 147.18 (C), 149.56 (CH), 149.67 (C), 155.35 (C), 155.47 (C).

EXAMPLE E

Preparation of 2-(2-pyridinyl)-4-carboxyquinoline acyl chloride 7

Thionyl chloride (20 ml) and benzene (30 mL) are added to a 100 mL round bottomed flask containing 2.0 g of 2-(2-pyridyl)-4-carboxyquinoline 4. The mixture is then heated at reflux for 90 minutes. The yellow/green solution is allowed to cool, and traces of the unreacted acid (4) are removed by filtration. Solvents are removed under reduced pressure giving 2.1 g of the title crude acid chloride. This is further dried under vacuum (~0.01 torr) for 1 hour. Fresh preparations of this compound can be used in subsequent reactions.

EXAMPLE F

Preparation of 2-(2-pyridinyl)-4-carboxyquinoline ethylene glycol ester 8.

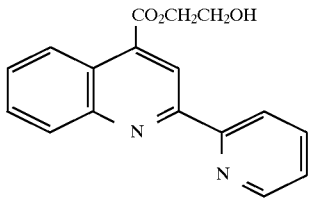

Ethylene glycol (50 mL) is added to a 100 mL round bottomed flask fitted with a magnetic stirring bar. With efficient stirring, the acid chloride 7 (prepared as detailed in Example E) is added to the ethylene glycol in small portions. The solution is allowed to stir for an additional 30 minutes. The solution is then poured into 300 mL of cold water, resulting in the immediate precipitation of a white solid. The mixture is made basic by the addition of solid sodium bicarbonate (foaming!), and filtered. The solid is allowed to dry, giving 3.6 g of the crude title product. Crystallization from ethanol gives 2.1 g of the title product, as a white solid.

$^1$H NMR (CDCl$_3$, 300 MHz): δ 3.60 (t, J=7.5 Hz, CH$_2$, 2H), 3.65 (Broad, 1H, OH), 4.50 (t, J=7.5 Hz, 2H, CH$_2$), 7.50 (dd, J=7.5, 4.8 Hz, 1H), 7.70 (dd, J=7.7, 7.5 Hz, 1H), 7.84 (dd, J=7.7, 7.5 Hz, 1H), 7.98 (dd, J=8.0, 7.5 Hz, 1H), 8.15 (d, J=8.4 Hz, 1H), 8.55 (d, J=8.0 Hz, 1H), 8.65 (d, J=8.4 Hz, 1H), 8.75 (d, J=4.8 Hz, 1H), 8.95 (s 1H).

$^{13}$C NMR (CDCl$_3$, 75 MHz): δ 58.77 (CH$_2$), 67.35 (CH$_2$), 119.12 (CH), 120.90 (CH), 124.00 (C), 124.59 (CH), 124.88 (CH), 125.17 (CH), 128.41 (CH), 129.78 (CH), 130.19 (CH), 135.85 (C), 137.37 (CH), 147.87 (C), 149.22 (CH), 154.04 (C), 154.85 (C), 165.67 (C=O), 206.31 (C).

EXAMPLE G

Preparation of (S) or (R)-2-(2-pyridinyl)-4-carboxyquinoline, methylbenzylamide 9

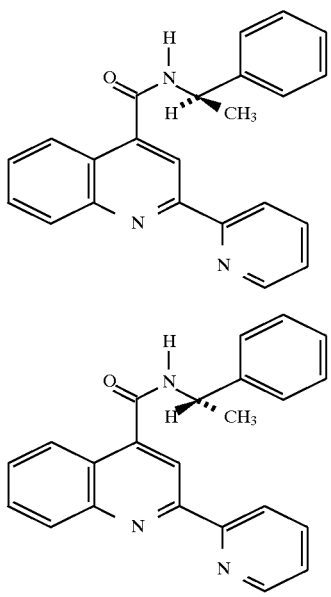

Freshly prepared acyl chloride 7 (prepared as described in Example E) (2.0 g, 7.5 mmole) is added to a solution containing triethylamine (2.0 g, 20 mmol) in 50 ml of dry chloroform. (S)- or (R)-methylbenzyl amine (0.9 g, 7.4 mmole) is then added in a single portion, with stirring. The solution is stirred for an additional 30 minutes at room temperature. The solvent is then removed under reduced pressure, and crystallization from hot benzene (carbon) yields the title product as a fluffy white solid (2.5 g). $^1$H NMR (DMSO, 300 MHz): δ 1.5 (vbs, 3H), 3.3 (vbs, 1H), 5.7 (vbs, 1H), 7.1–7.6 (vbm, 3H), 7.75 (vbs, 1H), 8.0 (vbs, 2H), 8.5 (vbs, 2H), 8.8 (vbs, 1H). $^{13}$C NMR (DMSO, 75 MHz): δ 22.69, 49.10, 116.44, 121.58, 124.77, 125.37, 125.71, 126.51, 127.29, 128.13, 128.83, 130.10, 130.68, 137.95, 143.80, 144.77, 148.01, 149.80, 155.07, 155.45, 166.37.

EXAMPLE H

General Procedure for the Preparation of N-[(2-(2-pyridinyl)-4-quinolinyl]carbonyl amino acids 10–18
SEE SCHEME II FOR FORMULA A solution is prepared containing 10 mmole of the amino acid or amino acid ester (for instance, 1.31 g leucine 1.45 g leucine methyl ester, 0.75 g glycine, 1.28 g of glycylglycine, 1.55 g histidine, 1.69 g histidine methyl ester, 1.32 g aspartic acid or 1.46 g glutamic acid), 50 mL of cold (5° C.) dry acetonitrile and 2.0 g of dry triethylamine. To this solution, with efficient stirring and while in an ice bath, is added 10 mmol (2.5 g) of freshly prepared acid chloride 7. Stirring is continued at 5° C. for 30 minutes, then the ice bath is removed and the solution stirred for an additional 8 hours. The desired amino acid coupled to the acyl group of the cinchonic acid acyl chloride product is collected by filtration, washed with acetonitrile (20 mL) and used in subsequent preparations without further purification. Yields are: (3.0 g Leucine, 3.2 g Leucine methyl ester, 2.0 g glycine, 2.5 g of glycyl glycine, 3.2 g Histidine, 3.4 g Histidine methyl ester, 3.6 g aspartic acid and 3.0 g glutamic acid derivatives).

EXAMPLE I

Preparation of 2,2'-bipyridine-4,4'-dicarboxylic acid, N,N-diethyl amide 38

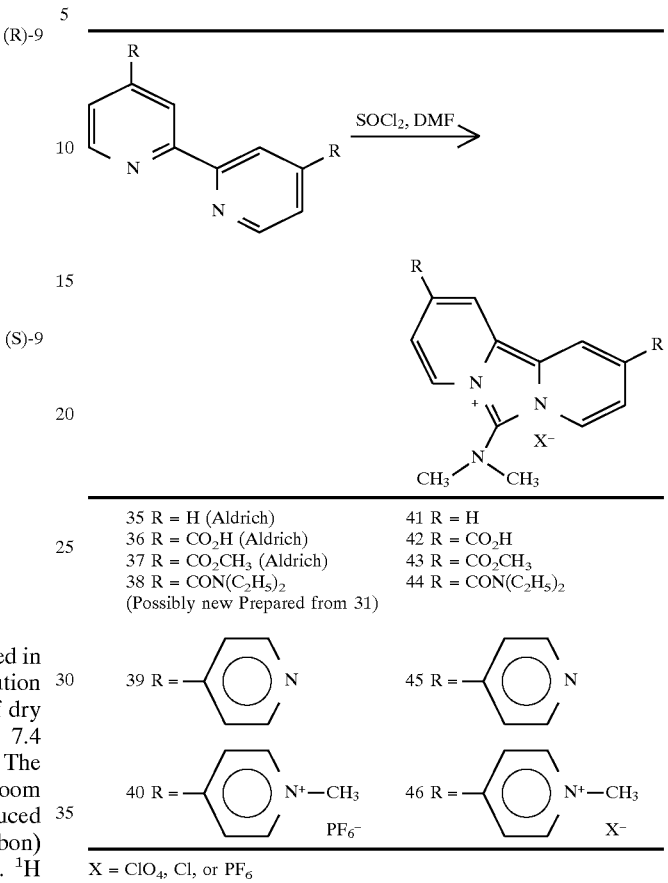

35 R = H (Aldrich)      41 R = H
36 R = CO$_2$H (Aldrich)  42 R = CO$_2$H
37 R = CO$_2$CH$_3$ (Aldrich) 43 R = CO$_2$CH$_3$
38 R = CON(C$_2$H$_5$)$_2$   44 R = CON(C$_2$H$_5$)$_2$
(Possibly new Prepared from 31)

39 R = —⟨phenyl⟩—N       45 R = —⟨phenyl⟩—N

40 R = —⟨phenyl⟩—N$^+$—CH$_3$  46 R = —⟨phenyl⟩—N$^+$—CH$_3$
              PF$_6^-$                    X$^-$ X = ClO$_4$, Cl, or PF$_6$ 2,2'-Bipyridine, 4,4'-dicarboxylic acid (1.0 g, 4.1 mol) is refluxed in 10 mL of thionyl chloride for 5 hours. The thionyl chloride is removed under reduced pressure, and added to 100 mL of toluene. The mixture is brought to a boil and filtered (gravity) into a cold stirring solution containing diethylamine (600 mg, 8.2 mmol), triethylamine (836 mg, 8.3 mmol) and 50 mL of toluene. The resulting solution is allowed to stir at room temperature for 30 minutes. The solution is poured into 100 mL of saturated sodium carbonate solution, and the layers are separated. The aqueous phase is extracted twice with 50 mL portions of chloroform. The extracts are combined with the toluene, and the volume reduced to about 10 mL by distillation. Heptane (50 ml) is added to the residue, and the resulting solid is filtered giving 2,2'-bipyridine-4,4'-dicarboxylic acid, N,N diethyl amide, as a low melting solid (500 mg).

EXAMPLE J

Preparation of 5,6-dipyridinyl 2,3-pyrazinedicarbonitrile 49 (Trival name: 2,3-dicyano-5,6-dipyridylpyrazine)

Into a 250 mL round bottomed flask are placed, 2,2'-pyridil (8.48 g, 40 mmol), diaminomaleonitrile (4.32 g, 40 mmol) and 125 mL of ethanol. The flask is fitted with a magnetic stirrer and a condenser, and refluxed for 30 minutes. The mixture is allowed to cool, and 10 mL of water is added. Filtration yielded 8.9 g of crude product as a beige solid. The solid is boiled in benzene (400 mL) and filtered hot. The red filtrate is discarded giving 5.2 g of the title compound as a pale beige solid.

EXAMPLE K

Preparation 2,3-dipyridyl-1,4,6-triazanaphthalene

Into a 50 mL round bottomed flask are placed, 0.515 g (4.0 mmol) of 3,4-diaminopyridine, 0.848 g (4.0 mmol) of 2,2-pyridil and 25 mL of ethanol (95%). With stirring, the mixture is refluxed for 30 minutes. The mixture is cooled, and treated with activated carbon, brought to a boil and filtered hot. Evaporation of the ethanol leaves a pale yellow oil, which slowly crystallized to give the title compound (500 mg) as a light yellow solid.

EXAMPLE L

Preparation of 2,3-dipyridyl-1,4,8-triazanaphthalene 62

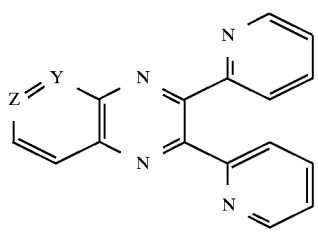

The preparation of 62 is identical to that of 61 substituting 2,3-diaminopyridine for 3,4-diamino pyridine (Example K), giving 900 mg of the title compound as a white solid.

PREPARATION OF COMPOUNDS OF THE INVENTION

EXAMPLE 1

Preparation of 5-carboxy-12-dimethylamino-pyrido[1',2':3,4]imidazo[1,5a]quinolin-11-ium acyl chloride perchlorate 19

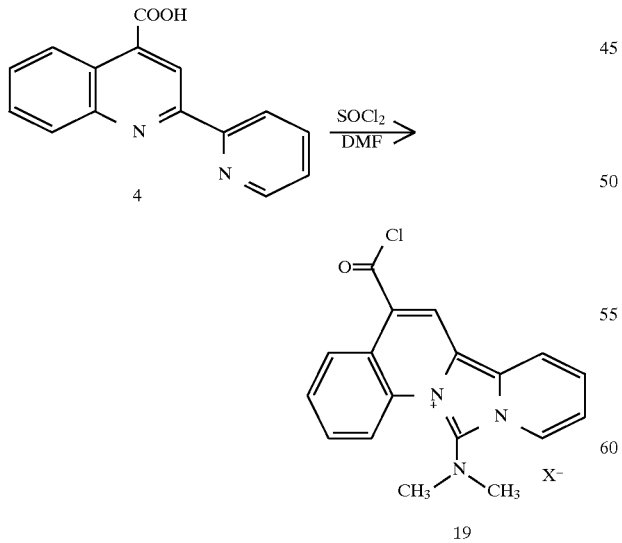

Thionyl chloride (40 mL) is placed in a 50 mL round bottomed flask, fitted with a magnetic stirring bar, and cooled to 5°–10° C. While in an ice bath, with stirring, 20 mmol (5.0 g) of 2-(2-pyridyl)-4-carboxyquinoline 4 (prepared as described in Example B) is added. The orange solution was allowed to stir in the ice bath for 15 minutes. The solution is then refluxed for 1 hour. The thionyl chloride is removed under reduced pressure. The deep orange red residue is then used in subsequent preparations without further purification.

EXAMPLE 2

General Procedure for the Preparation of Fluorescent Cinchonic Acid Derivatives

Thionyl chloride (40 mL) is placed in a 50 mL round bottomed flask, fitted with a magnetic stirring bar, and cooled to 5°–10° C. While in an ice bath, with stirring, 20 mmol of the cinchonic acid derivative (5.0 g 4, 5.4 g of 5, 4.72 g of 6, 5.88 g of 8, 7.0 g of 9 (R) or (S)) is added. In a single portion, 40 mmol (2.92 g) of dimethylformamide (DMF) is added, producing an immediate color change (in the preparation of 23 the solution is refluxed for 15 minutes). The orange solution is then allowed to stir in the ice bath for an additional 15 minutes. The ice bath is removed and the solution is stirred for a further 30 minutes. The thionyl chloride is removed under reduced pressure, and the solid is dissolved in 100 mL of water. The solution is filtered, and 4 g of solid sodium perchlorate is added, producing a bright yellow precipitate. The mixture is cooled to 5° C., and the solid filtered. The solid can be recrystallized from methanol giving the perchlorate salts 20–25 as a yellow solids.

A. Preparation of 5-carboxy-12-dimethylamino-pyrido[1',2':3,4,]imidazo[1,5-a]quinolin-11-ium perchlorate 20

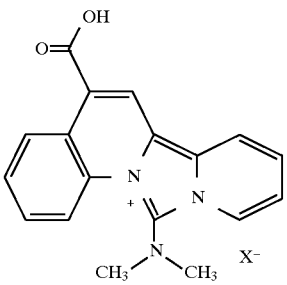

yield: 8.1 g, $^{13}$C NMR: (DMSO-d$_6$) δ 39.46, 114.56, 117.59, 118.09, 119.25, 120.32, 120.87, 121.90, 122.73, 122.96, 126.44, 127.26, 128.80, 130.26, 131.37, 166.63. MS m/z (positive in FAB) 306.1240, [M$^+$] Calcd. for (C$_{18}$H$_{16}$N$_3$O$_2$PF$_6$) 306.124251. Anal. Calcd. for C$_{18}$H$_{16}$B$_3$O$_2$PF$_6$C, 47.9; H, 3.6; N, 9.3. Found: C, 48.17; H, 226; N, 93.

B. Preparation of 5-methoxycarbonyl-12-dimethylamino-pyrido[1',2':3,4]imidazo[1,5-a]quinolin-11-ium perchlorate 21

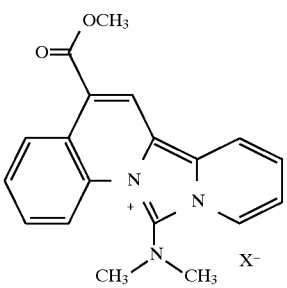

yield: 8.2 g, NMR: $^1$H(300 MHz, DMSO-d$_6$): δ 3.25 (s, 6H), 4.0 (s, 3H), 7.65 (dd, J=6.9, 6.8 Hz, 1H), 7.68 (dd, J=6.9, 6.8 Hz, 1H), 7.85 (dd, J=7.6, 7.3 Hz, 1H), 7.95 (dd, J=7.9, 7.6 Hz, 1H), 8.80 (d, J=9.7 Hz, 1H), 8.85 (dd, J=9.7, 7.9, 1H), 8.95 (d, J=8.6 Hz, 1H), 9.05 (s, 1H). $^{13}$C (DMSO-$d_6$): δ 39.5, 54.0, 116.1, 119.06, 119.09, 120.46, 121.07, 121.24, 122.84, 123.60, 124.01, 126.54, 127.45, 129.32, 130.22, 130.45, 132.70, 166. MS m/z (positive ion FAB) 320.21, [M$^+$], Calcd. for ($C_{19}H_{18}N_3O_2$) 320.1399.

C. Preparation of 5-methoxy-12-dimethylamino-pyrido[1',2':3,4]imidazo [1,5-a]quinolin-11-ium perchlorate 22 yield: 6.4 g,

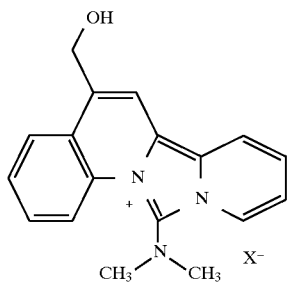

22

D. Preparation of 5-chlorethoxycarbonyl-12-dimethylamino-pyrido[1',2':3,4]imidazo[1,5-a]quinolin-11-ium perchlorate 23:

yield 8.4 g,

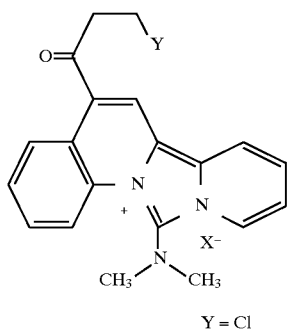

23

Y = Cl

E. Preparation of 5-carboxy-12-dimethylamino-pyrido[1', 2':3,4]imadizo[1,5-a]quinolin-11-ium 5(R)-methylbenzylamide perchlorate 24:

yield 9.4 g,

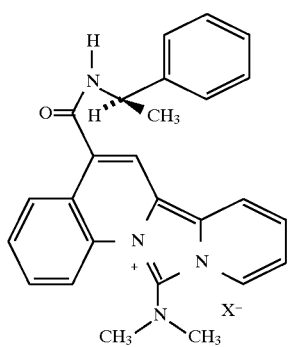

24

F. Preparation of 12-diemethylamino-5-carboxy-pyrido[1', 2':3,4]imidazo[1,5-a]quinolin-11-ium 5(S)-methylbenzylamide perchlorate. 25 yield 9.3 g.

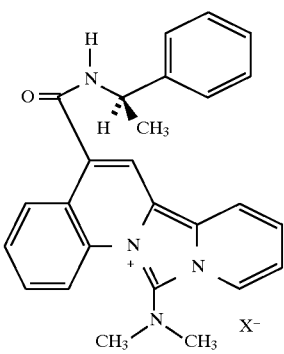

25

G. Using N,N-diethylformamide in place of the N,N-dimethylformide, and repetition of the above procedure, there is produced 5-carboxy-12-diethylamino-pyrido[1',2':3, 4]imidazo[1,5-a]quinolin-11-ium perchlorate, NMR: $^1$H (300 MHz, DMSO-$d_6$): δ 1.14 (t, J=7.1 Hz, 6H), 3.6 (m, 4H), 7.6 (dd, J=6.8, 6.8 Hz, 1H), 7.65 (dd, J=6.8, 6.8 Hz, 1H), 7.85 (dd, J=7.6, 7.6 Hz, 1H), 7.95 (dd, J=7.6, 7.6 Hz, 1H), 8.8 (d, J=6.8 Hz, 1H), 8.88 (d, J=8.6 Hz, 1H), 9.1 (s, 1H), 9.15 (d, J=8.6 Hz, 1H). $^{13}$C (DMSO-$d_6$) δ 13.91, 45.89, 117.05, 118.63, 119.32, 120.94, 122.43, 122.66, 123.57, 124.50, 126.29, 127.98, 129.33, 130.08, 130.36, 130.78, 166.91.

H. Using an equivalent amount of N,N-dibutylformamide in place of the N,N-dimethylformamide, there is produced 5-carboxy-12-dibutylamino-pyrido[1',2':3,4]imidazo[1,5-a] quinolin-11-ium perchlorate NMR: $^1$H (300 MHz, DMSO-$d_6$) δ 0.78 (t, J=7.3 Hz, 6H), 1.15 (q, J=7.3, 4H), 1.55 (m, 4H), 3.75 (m, 4H), 7.55 (dd, J=6.8, 6.8 Hz, 1H), 7.60 (dd, J=6.8, 6.8 Hz, 1H), 7.85 (dd, J=8.0, 7.3 Hz, 1H), 7.95 (dd, J=7.3, 7.3 Hz, 1H), 8.70 (d, J=6.8 Hz, 1H), 8.78 (d, J=8.6 Hz, 1H), 8.95 (d, J=8.0 Hz, 1H), 9.02 (s, 1H), 9.05 (d, J=8.6 Hz, 1H). $^{13}$C (DMSO-$d_6$) d 14.00, 20.03, 30.50, 51.68, 116.93, 118.78, 119.21, 120.86, 122.34, 122.52, 123.46, 124.49, 126.19, 127.87, 129.27, 130.01, 130.33, 131.13, 166.93.

EXAMPLE 3

General Procedure for the Preparation of Fluorescent 5-(Amino acid)-12-dimethylamino-pyridyl[1',2':3,4]imidazo[1,5-a]quinolin-11-ium Derivatives 26–34

Thionyl chloride (5 mL) is placed in a 25 mL round bottomed flask, fitted with a magnetic stirring bar, and cooled to 5°–10° C. While in an ice bath, with stirring, 1 mmol the cinchoninic acid derivative (307 mg of 10, 321 mg of 11, 363 mg of 12, 370 mg of 13, 388 mg of 14, 401 mg of 15, 364 mg of 16, 365 mg of 17, 379 mg of 18) is added. In a single portion, 4 mmol (292 mg) of dimethyl formamide is added, producing an immediate color change. The orange solution is allowed to stir in the ice bath for 15 minutes. The ice bath is then removed and the solution is stirred for an additional 30 minutes. The thionyl chloride is removed under reduced pressure, and the solid is dissolved in 25 mL of water. The solution is filtered, and 2 g of solid sodium perchlorate is added, producing a bright yellow precipitate. The mixture is cooled to 5° C., and the solid filtered. The solid can be recrystallized from methanol giving the perchlorate salts 26–34 as yellow solids.

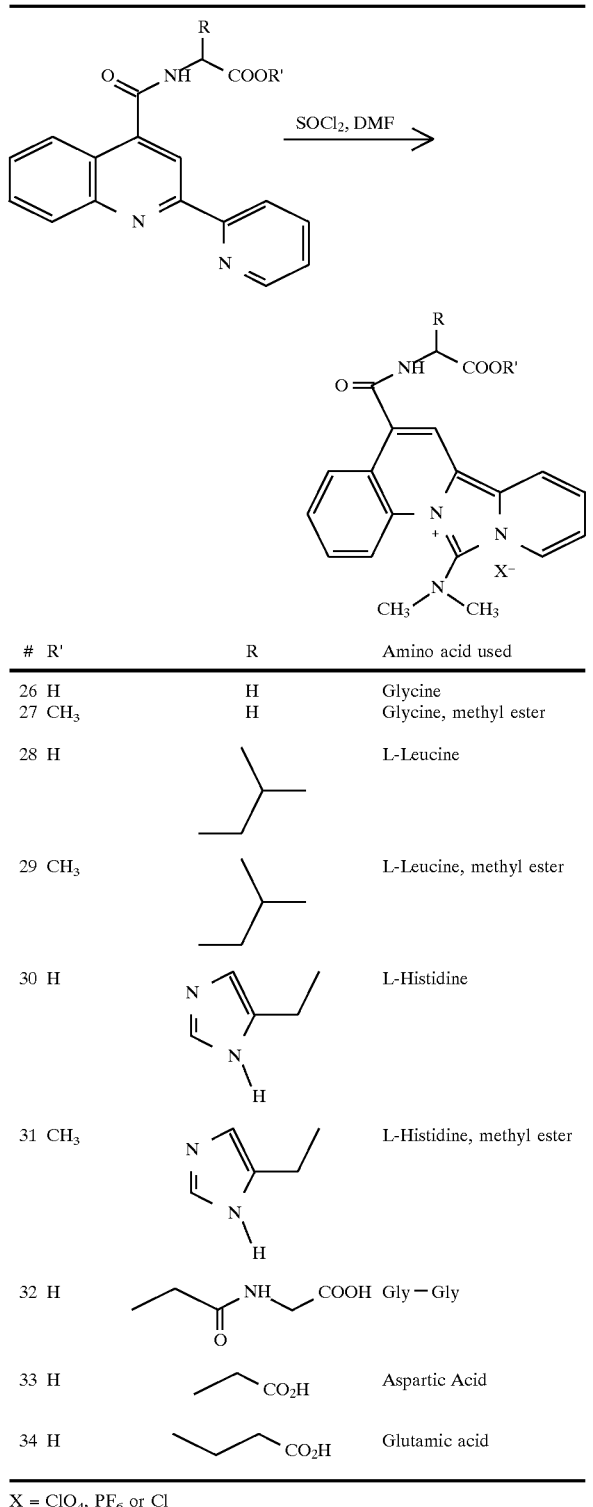

| # | R' | R | Amino acid used |
|---|---|---|---|
| 26 | H | H | Glycine |
| 27 | CH₃ | H | Glycine, methyl ester |
| 28 | H | isobutyl | L-Leucine |
| 29 | CH₃ | isobutyl | L-Leucine, methyl ester |
| 30 | H | imidazolylmethyl | L-Histidine |
| 31 | CH₃ | imidazolylmethyl | L-Histidine, methyl ester |
| 32 | H | CH₂CH₂C(O)NHCH₂COOH | Gly—Gly |
| 33 | H | CH₂CO₂H | Aspartic Acid |
| 34 | H | CH₂CH₂CO₂H | Glutamic acid |

X = ClO₄, PF₆ or Cl

Yields: 5-(L-glycyl)-12-dimethylamino-pyridyl[1',2':3,4]imidazo[1,5-a]quinolin- 11-ium perchlorate 26: 550 mg, NMR: ¹H (300 MHz, DMSO-$d_6$) δ 3.5 (s,6H), 4.5 (d, J=7.7 Hz, 1H), 4.55 (d, J=7.7 Hz, 1H), 7.25 (m, 1H), 7.30 (m, 1H), 7.85 (m, 1H), 7.95 (m, 1H), 8.22 (d=j 7.0 Hz, 1H), 8.35 (m, J=7.0 Hz, 1H), 8.85 (m, 3H). ¹³C NMR (75 MHz, DMSO-$d_6$), DEPT (90) Correlations) δ 39.33 (CH₃), 61.93 (CH₂), 118.07 (CH), 118.28 (CH), 119.97 (CH), 120.04 (CH), 1211.59 (CH), 127.62 (CH), 128.82 (CH), 128.85 (CH), 129.81 (CH), 129.90 (CH).

5-(L-glycylmethylester)-12-dimethylamino-pyridyl[1',2':3,4]imidazo[1,5-a]quinolin-11-ium-perchlorate 27: 540 mg, 5-(L-leucinyl)-12-dimethylamino-pyridyl[1',2':3,4]imidazo[1,5-a]quinolin-11-ium-perchlorate 28: 600 mg, 5-(L-leucinemethyl ester)-12-dimethylamino-pyridyl[1', 2':3,4]imidazo[1,5-a]quinolin-11-ium-perchlorate 29: 470 mg, 5-(L-histidinyl)-12-dimethylamino-pyridyl[1',2':3,4]imidazo[1,5-a]quinolin-11-ium-perchlorate 30 550 mg, NMR:¹H (300 MHz, DMSO-$d_6$) δ 3.3 (s, 6H), 3.75 (m, 2H), 4.00 (s, 3H), 5.10 (m, 1H), 7.55 (m, 2H), 7.80 (m, 1H), 7.95 (m, 2H), 8.12 (s, 2H), 8.15 (s, 2H), 8.40 (s, 1H), 8.55 (m, 1H)m 8.90 (m, 1H). ¹³C NMR (75 MHz, DMSO-$d_6$,DEPT (90) correlations) δ 25.87, 39.01, 51.65, 52.42, 115.07, 117.49, 118.13, 118.35, 119.83, 121.27, 121.99, 123.59, 124.92, 126.98, 128.73, 129.23, 129.79, 130.17, 133.81, 164,23, 166.51, 170.38.

(L-histidinylmethyl ester)-12-dimethylamino-pyridyl[1', 2':3,4]imidazo[1,5-a]quinolin-11-ium-perchlorate 31: 666 mg, 5-(L-glycylglycyl)-12-dimethylamino-pyridyl[1',2':3,4]imidazo[1,5-a]quinolin-11-ium-perchlorate 32: 550 mg, 5-(L-glutamyl)-12-dimethylamino-pyridyl[1',2':3,4]imidazo[1,5-a]quinolin-11-ium-perchlorate 34: 610 mg.

EXAMPLE 4

Preparation of Fluorescent Bipyridine Derivatives 41–46

A. 6-(dimethylamino)-dipyrido[1,2-c:2',1'-e]imidazol-5-ium perchlorate 41

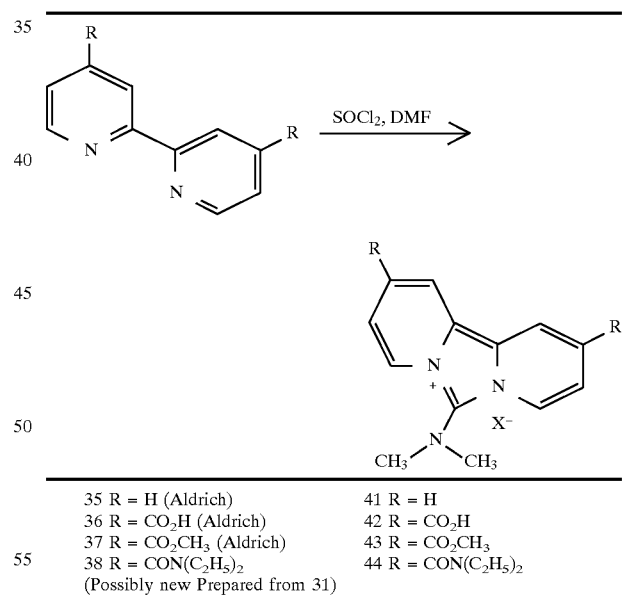

| 35 R = H (Aldrich) | 41 R = H |
| 36 R = CO₂H (Aldrich) | 42 R = CO₂H |
| 37 R = CO₂CH₃ (Aldrich) | 43 R = CO₂CH₃ |
| 38 R = CON(C₂H₅)₂ | 44 R = CON(C₂H₅)₂ |
| (Possibly new Prepared from 31) | |

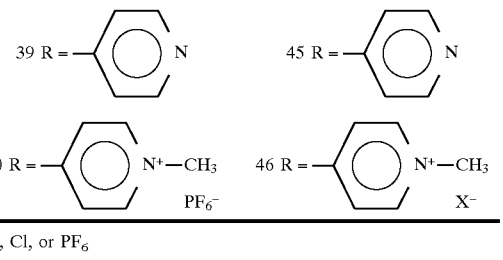

X = ClO₄, Cl, or PF₆

A solution of 2,2'-bipyridine 35 (1.0 g, 6.4 mmol) in 25 mL of benzene is cooled to 0° C. in an ice bath. To a solution containing 800 mg (6.78 mmol) of thionyl chloride in 5 mL of benzene is added 495 mg of DMF (4.95 mmol) in a single portion. Both solutions are stirred for 5 minutes. The mixture of DMF/thionyl chloride is added to the 2,2' bipyridine solution with stirring in a single portion. The addition produces a yellow solution containing an oily brown residue. The reaction is stirred for an additional 15 minutes at 0° C., and then the ice bath is removed, and stirring is continued for an additional 30 minutes. As the DMF is consumed, the oily brown residue gradually solidifies. The solid is filtered, and allowed to dry. The precipitate is dissolved in water, and filtered. The addition of 5 g of solid sodium perchlorate produces the immediate formation of a bright yellow precipitate (1.7 g). The precipitate is dried, and chromatographed on alumina (neutral, Brockman Activity I) elution with acetonitrile. The salt elutes as a broad yellow band, recrystallization from ethanol (sparingly soluble and acetonitrile (soluble), yields 1.5 g (75%) of 1 as a yellow crystalline solid. NMR: $^1$H (300 MHz, DMSO-d$_6$) δ 3.14 (s, 6H), 7.49 (m, 4H), 8.61 (d, J=8.89 Hz, 2H), 8.67 (d, J=7.17 Hz, 2H). $^{13}$C (75 MHz, DMSO-d$_6$) δ 40.00, 119.32, 119.34, 120.45, 121.30, 122.33, 127.15. IR (KBr) cm$^{-1}$ 1658, 1616, 1646, 1561, 1543, 1429. MS m/z (positive ion FAB) 212.0 [M]$^+$, Calcd. for (C$_{13}$H$_{14}$N$_3$) 212.1. Anal. Calcd for C$_{13}$H$_{14}$N$_3$O$_4$Cl: C, 50.1; H, 4.5; N 13.5. Found: C, 49.89; H, 4.21; N, 13.66.

B. 6-(dimethylamino)-2-10-bis(carboxy)-dipyrido[1,2-c:2',1'-e]imidazol-5-ium perchlorate 42

Thionyl chloride (5 mL) is added to a 25 mL round bottom flask containing a stirring bar. The flask is cooled to 0°–5° C. in an ice bath, and 550 mg (2.3 mmol) of 36 is added. The mixture is again brought to 5° C. To the stirring solution, 150 mg (2.1 mmol) is added in a single portion. The ice bath is removed, and the solution is stirred for 1 hour. The orange solution is cooled to room temperature, and the excess thionyl chloride removed under reduced pressure (~0.1 torr). The residue is dissolved in 125 mL of water, brought to a boil, and filtered while hot. The addition of 1 g of sodium perchlorate resulted in the immediate precipitation of title compound 42 as a yellow salt. The mixture is cooled to 5° C. and filtered. Recrystallization from methanol yielded 400 mg (41%) of the title compound as orange crystals. NMR: $^1$H (300 MHz, DMSO-d$_6$) δ 3.20 (s, 6H), 7.84 (dd, J=7.37, 0.86 Hz, 2H), 8.76 (d, J=7.37 Hz, 2H), 9.52 (bs, 2H). $^{13}$C (300 MHz, DMSO-d$_6$) δ 118.52, 120.80, 121.72, 122.38, 124.87, 130.02, 165.20. IR (KBr) cm$^{-1}$ 1721(C=O) 1626, 1563, 1452, 1428, 1327, 1276, 1258. MS m/z (positive ion FAB) 300.1, [M]$^+$, Calcd. for (C$_{15}$H$_{14}$N$_3$O$_4$) 300.1. Anal. Calcd. for C$_{15}$H$_{14}$N$_3$O$_8$Cl: H$_2$OC, 43.1; H, 3.9; N, 10.1. Found: C, 43.12; H, 3.79; N, 9.99.

C. 6-(dimethylamino)-2,10-bis(methoxycarbonyl)-Dipyrido[1,2-c:2',1'-e]imidazol-5-ium perchlorate 43

Thionyl chloride (5 mL) is added to a 25 mL round bottom flask containing a stirring bar. The flask is cooled to 0°–5° C. in an ice bath, and 410 mg (1.5 mmol) of 5,5'-dimethylamino carbonyl-2,2'-bipyridine 37 is added. To the stirring solution, 150 mg of DMF (2.1 mmol) is added in a single portion. The ice bath is removed; the solution is stirred for 30 minutes, and finally brought to a boil. The orange solution is cooled to room temperature, and the excess thionyl chloride removed under reduced pressure (~0.1 torr). The residue is dissolved in 75 mL of water, and any solids removed by filtration. The addition of 3 g of sodium perchlorate resulted in the immediate precipitation of 43 as yellow salt. Recrystallization from methanol yielded 500 mg (78%) of the title compound as orange crystals. NMR: $^1$H (300 MHz, DMSO-d$_6$) δ 3.21 (s, 6H), 4.00 (s, 6H), 7.87 (bd, J=7.31 Hz, 2H), 8.80 (d, J=7.38 Hz, 2H), 9.65 (bs, 2H). $^{13}$C (75 MHz, DMSO-d$_6$) δ 39.51, 52.94, 118.08, 120.87, 122.01, 122.59, 123.66, 130.46, 164.14. IR (KBr) cm–1 1719, 1622, 1561, 1438, 1327, 1254, 1093. IR (KBr) cm–1 1719, 1622, 1561, 1438, 1327, 1254, 1093. MS m/z (positive ion FAB) 328.1, [M]+, Calcd. for (C$_{17}$H$_{18}$N$_3$O$_4$) 328.1. Anal. Calcd. for C$_{17}$H$_{18}$N$_3$O$_8$Cl C, 47.7; H, 4.2; N, 9.8. Found C, 47.68; H, 4.21; N, 9.82.

D. 6-(dimethylamino)-2,10-bis(diethylaminocarbonyl)-dipyrido[1,2-c:2',1'-e]imidazol-5-ium hexafluorphosphate 44

Thionyl chloride (10 mL) is placed in a 25 mL round bottomed flask, fitted with a magnetic stirring bar, and cooled to 5°–10° C. While in an ice bath, with stirring, 354 mg (1 mmol) of 38 (prepared as described in Example I) is added. In a single portion, 4 mmol (292 mg) of DMF is then added, producing an immediate color change. The orange solution is allowed to stir in the ice bath for 15 minutes. The ice bath is then removed and the solution is stirred for an additional 30 minutes. The thionyl chloride is removed under reduced pressure, and the solid is dissolved in 50 mL of water. The solution is filtered, and 2 g of solid ammnonium hexafluorophosphate is added, producing a bright orange precipitate. The mixture is cooled to 5° C. and the solid filtered. The solid can be recrystallized from methanol giving the hexafluorophosphate salt 44 as an orange solid (420 mg).

E. 6-(dimethylamino)-2,10-bis(2'-pyridyl)-dipyrido[1,2-c:2',1'-e]imidazol-5-ium hexafluorphosphate 45

Thionyl chloride (10 mL) is placed in a 25 mL round bottomed flask, fitted with a magnetic stirring bar, and cooled to 5°–10° C. While in an ice bath, with stirring, 310 mg (1 mmol) of the quaterpridine 39 is added. In a single portion, 4 mmol (292 mg) of DMF is added, producing an immediate color change. The orange solution is allowed to stir in the ice bath for 15 minutes. The ice bath is then removed and the solution is stirred for an additional 30 minutes. The thionyl chloride is removed under reduced pressure, and the solid is dissolved in 50 mL of water. The solution is filtered, and 2 g of solid ammonium hexafluorophosphate is added, producing a bright yellow/orange precipitate. The mixture is cooled to 5° C., and the solid filtered. The solid is then chromatographed on alumina (acetonitrile eluent) giving the title compound (350 mg) as an orange/yellow solid.

F. Preparation of Fluorescent Quaterpyridinium Adduct 46

Thionyl chloride (10 mL) is placed in a 25 mL round bottomed flask, fitted with a magnetic stirring bar, and cooled to 5°–10° C. While in an ice bath, with stirring, 1 mmol of 40 (as its bis PF$_6^-$ salt, 630 mg) is added. In a single portion, 4 mmol (292 mg) of DMF is added, producing an immediate color change. The purple/red solution is allowed to stir in the ice bath for 15 minutes. The ice bath is then removed and the solution is stirred for an additional 30 minutes. The thionyl chloride is removed under reduced pressure, and the solid is dissolved in 50 mL of water. The solution is filtered, and 2 g of solid ammonium hexafluorophosphate is added, producing a deep purple precipitate. The mixture is cooled to 5° C., and the solid filtered. The solid can be recrystallized from methanol giving the hexafluorphosphate salt 46 as a deep purple solid (750 mg).

EXAMPLE 5

A. Preparation of 6-(dimethylamino)-1-(2-pyridinyl)-pyrido[1',2':3,4]imidazo[1,5-a]pyrazin-5-ium perchlorate 52

(monomeric dpp)

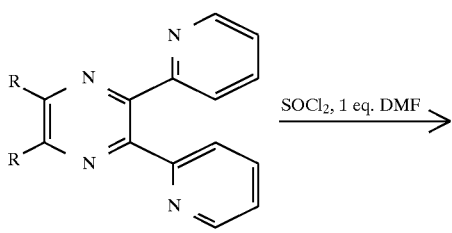

50 R = H (Aldrich)
51 R = CH₃ (Aldrich)

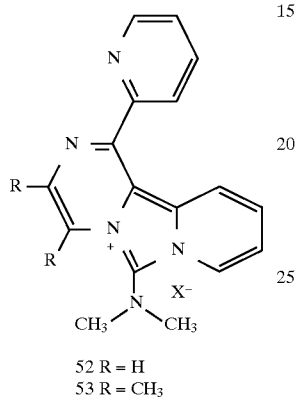

52 R = H
53 R = CH₃

A 25 mL round bottomed flask containing 10 mL of thionyl chloride is cooled to 5° C. in an ice bath. To the flask is added 2,3-bis-(2-dipyridyl)pyrazine 50 (468 mg, 2.0 mmole), and the mixture stirred for 5 minutes. DMF (146 mg, 2.0 mmole) is added dropwise over a period of 20 minutes, and the orange solution stirred for an additional 30 minutes. The thionyl chloride is removed under reduced pressure (~0.1 torr, 25° C.). The resulting red solid is dissolved in 150 mL of water, and precipitated by the addition of 2 g of ammonium hexafluorophosphate. The resulting yellow solid is filtered and dried. Column chromatography (Alumina neutral, acetonitrile) can be used to remove traces of the dimer (54). The deep yellow band is collected and recrystallized from methanol (sparingly soluble) and acetonitrile (soluble). The procedure gives 52 as a yellow solid (300 mg): NMR: $^1$H (300 MHz, DMSO-d$_6$) δ 3.45 (s, 6H), 7.68 (m, 2H), 7.80 (m, 1H), 7.95 (m, 3H), 8.20 (m, 3H), 8.85 (m, 1H), 8.88 (d, J=2.1 Hz, 1H), 8.98 (m, 1H). $^{13}$C (75 MHz, DMSO-d$_6$) δ 39.64, 116.28, 118.88, 119.15, 120.38, 120.86, 122.26, 122.62, 123.29, 124.39, 126.16, 127.76, 129.15, 130.22, 132.41, 166.83. E.A.

B. Preparation of 6,11-di(dimethylamino)-bispyrido[1',2':3,4]imidazo[1,5-a:5',1'-c]pyrazine-5,10-diium diperchlorate 53 (monomeric dimethyl dpp)

A 25 mL round bottomed flask containing 10 mL of thionyl chloride is cooled to 5° C. in an ice bath. To the flask is added 51 (524 mg, 2.0 mmole), and the mixture stirred for 5 minutes. DMF (146 mg, 2.0 mmole) is added in a single portion, and the orange solution stirred for an additional 30 minutes. The thionyl chloride is removed under reduced pressure (~0.1 torr, 25° C.). The resulting red solid is dissolved in 150 mL of water, and precipitated by the addition of 2 g of ammonium hexafluorophosphate. The resulting yellow solid is filtered and dried. Column chromatography (alumina neutral, acetonitrile) can be used to remove traces of the dimer (55). The deep yellow band is collected and recrystallized from methanol (sparingly soluble) and acetonitrile (soluble). The procedure gives 53 as a yellow-orange solid (350 mg). NMR: $^1$H (300 MHz, DMSO-d$_6$) δ 3.55 (s, 6H), 7.40 (dd, J=7.3, 7.3 Hz, 2H), 7.52 (dd, J=9.0, 7.3 Hz, 2H), 8.38 (s, 2H), 8.50 (d, j=9.0, 2H), 8.60 (d, J=7.3 Hz, 2H). $^{13}$C (75 MHz, DMSO-d$_6$) δ 40.81 (CH₃), 106.653 (C), 114.252 (CH), 118.727 (CH), 119.144 (CH), 120.347(C), 123.599 (CH), 126.421 (CH), 134.338 (C).

EXAMPLE 6

A. Preparation of dimeric dpp 54

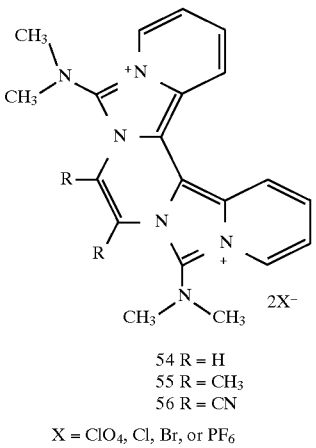

54 R = H
55 R = CH₃
56 R = CN

X = ClO₄, Cl, Br, or PF₆

A 25 mL round bottomed flask containing 10 mL of thionyl chloride is cooled to 5° C. in an ice bath. To the flask is added 2,3-bis-(2-dipyridyl)pyrazine 50 (468 mg, 2.0 mmole), and the mixture stirred for 5 minutes. N,N-dimethyl formamide (DMF) (584 mg, 8.0 mmole) is added in a single portion, and the orange solution stirred for an additional 30 minutes. The thionyl chloride is removed under reduced pressure (~0.1 torr, 25° C.). The resulting red solid is dissolved in 150 mL of water, and precipitated by the addition of 2 g of ammonium hexafluorophosphate. The resulting yellow solid is filtered and dried. Recrystallization from methanol (sparingly soluble) and acetonitrile (soluble). The procedure gives 54 as a yellow solid (700 mg).

B. Preparation of Dimeric dimethyl dpp 55

A 25 mL round bottomed flask containing 10 mL of thionyl chloride is cooled to 5° C. in an ice bath. To the flask is added 51 (524 mg, 2.0 mmole), and the mixture stirred for 5 minutes. N,N-dimethyl formamide (DMF) (584 mg, 8.0 mmole) is added in a single portion, and the orange solution stirred for an additional 30 minutes. The thionyl chloride is removed under reduced pressure (~0.1 torr, 25° C.). The resulting red solid is dissolved in 150 mL of water, and precipitated by the addition of 2 g of ammonium hexafluorophosphate. Recrystallization from methanol (sparingly soluble) and acetonitrile (soluble). The procedure gives 55 as a yellow-orange solid (680 mg).

C. Preparation of dimeric dicyano dpp 56

A 25 mL round bottomed flask containing 10 mL of thionyl chloride is cooled to 5° C. in an ice bath. To the flask is added 5,6-dipyridinyl-2,3-pyrzainedicarbonitrile 49 (572 mg, 2.0 mmole, prepared as described in Example J), and the mixture stirred for 5 minutes. N,N-dimethyl formamide (DMF) (584 mg, 8.0 mmole) is added in a single portion, and the orange solution stirred for an additional 30 minutes. The thionyl chloride is removed under reduced pressure (~0.1 torr, 25° C.). The resulting red solid is dissolved in 150 mL of water, and precipitated by the addition of 2 g of ammonium hexafluorophosphate. Recrystallization from methanol (sparingly soluble) and acetonitrile (soluble). The procedure gives 56 as a yellow-orange solid (650 mg).

EXAMPLE 7

Preparation of 12-(dimethylamino)-6-(2-pyridinyl)-pyrido[1'2':3,4]imidazo[1,5-a]quinoxalin-11-ium perchlorate 63 (quin momer)

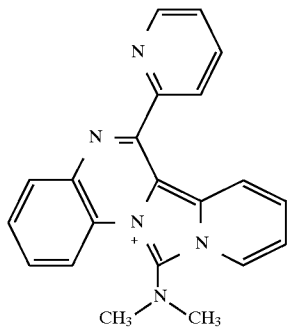

63

Thionyl chloride (10 mL) is added to a 25 mL round bottom flask in an ice bath. To the flask is added 500 mg (1.76 mmole) of 2,3-dipyridylquinoxaline 60, and the mixture stirred for 5 minutes. Dimethyl formamide (129 mg, 1.76 mmole) is added to the flask a single portion, and the orange solution stirred for 30 minutes. The thionyl chloride is removed under reduced pressure (~0.1 torr, 25° C.). The resulting red solid is dissolved in 150 mL of water, and precipitated by the addition of 3 g of ammonium hexafluorophosphate. Column chromatography (Alumina neutral, acetonitrile) can be used to remove traces of the dimer (64). The resulting yellow/orange solid is filtered, dried, and recrystallized from a mixture of methanol (sparingly soluble) and acetonitrile yielding 470 mg of 63 as an orange crystalline solid. NMR: $^1$H (400 MHz, DMSO-d$_6$) δ 3.27 (s, 6H), 7.68 (m, 2H), 7.81 (m, 1H), 7.99 (m, 3H), 8.21 (m, 3H), 8.86 (m, 2H), 8.98 (m, 1H). $^{13}$C NMR (400 MHz, DMSO-d$_6$, DEPT (90) correlations) δ 38.36 (CH$_3$), 109.15 (C), 116.94 (CH), 118.62 (CH), 119.29(CH), 121.75 (CH), 121.83 (C), 122.65(C), 123.45 (CH), 125.08 (CH), 126.75 (CH), 129.01 (CH), 129.10 (CH), 129.20 (CH), 131.65 (C), 136.45 (C), 137.26 (CH), 147.96 (CH), 150.75 (C), 153.14 (C). FABMS Calcd. for C$_{21}$H$_{18}$ N$_5$=340.40. Found: 340.24.

EXAMPLE 8

A. Preparation of Quin dimer 6,13-bis-(dimethylamino)-Bispyrido[1',2':3,4]imidazo[1,5-a:5'1'-c]quinoxalin-5,12-diium diperchlorate 64

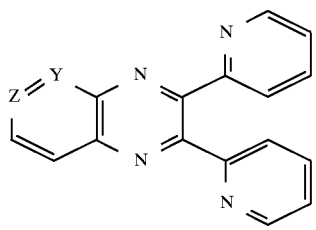

60 Y = Z = CH (Aldrich)
61 Y = CH, Z = N (New)
62 Y = N, Z = CH (New)

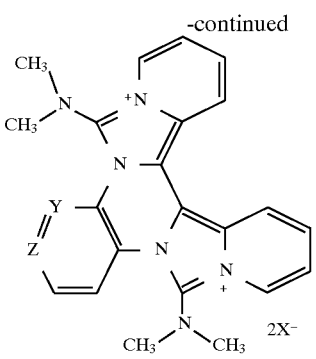

64 Y = Z = CH
65 Y = CH, Z = N
66 Y = N, Z = CH

Thionyl chloride (10 mL) is added to a 25 mL round bottom flask in an ice bath. To the flask is added 500 mg (1.76 mmole) of 2,3-dipyridylquinoxaline 60, and the mixture stirred for 5 minutes. Dimethyl formamide (514 mg, 7.0 mmole) is added over a period of 20 minutes, and the orange solution stirred for 30 minutes. The thionyl chloride is removed under reduced pressure (~0.1 torr, 25° C.). The resulting red solid is dissolved in 150 mL of water, and precipitated by the addition of 3 g of ammonium hexafluorophosphate. The resulting yellow solid is filtered, and recrystallized from a mixture of methanol (sparingly soluble) and acetonitrile (soluble), yielding 700 mg of 64 as a red crystalline solid. NMR: $^1$H (400 MHz, DMSO-d$_6$) δ 3.22 (s, 12H), 7.41 (dd, J=7.0, 6.8 Hz, 2H), 7.55 (dd, J=9.5, 6.8 Hz, 2H), 8.00 (dd, J=6.5, 3.5 Hz, 2H), 8.43 (dd, J=6.5, 3.5 Hz, 2H), 8.47 (d, J=9.5 Hz, 2H), 8.65 (d, J=7.0 Hz, 2H). $^{13}$C NMR (75 MHz, DMSO-d$_6$, DEPT (90) correlations) δ 38.38 (CH$_3$), 110.26 (C), 121.43 (CH), 121.73 (CH), 123.13 (CH), 123.52 (C), 126.36 (CH), 127.07 (C), 129.92 (CH), 133.62 (CH), 138.66 (C). FABMS Calcd. for C$_{24}$H$_{24}$N$_6$=396.49. Found=396.30.

B. Preparation of β-azo-dpp dimer 65

The preparation of 65 is identical to that of 64 (above), using 2,3-di(2-pyridyl)-1,4,9-triazanapthalene giving 450 mg of 65 as a red solid.

C. Preparation of α-azo-dpp dimer 66

The preparation of 65 is identical to that of 64 (above), using 2,3-di(2-pyridinyl)-1,4,8-triazanaphthalene giving 600 mg of 66 as a red solid.

EXAMPLE 9

Preparation of diaza Anthracene monomer: 13-(dimethylamino)-7-(2-pyridinyl)-benzo[g]-pyrido[1', 2':3,4]imidazo[1,5-a]quinoxalin-12-ium perchlorate 68

Thionyl chloride (10 mL) is added to a 25 mL round bottom flask in an ice bath. To the flask is added 664 mg (2.0 mmole) of 2,3-dipyridinyl-benzo[g]quinoxaline 67, and the mixture stirred for 5 minutes. Dimethyl formamide (146 mg, 2.0 mmole) is added to the flask dropwise over a period of 20 minutes, and the red solution stirred for 30 minutes. The thionyl chloride is removed under reduced pressure (~0.1 torr, 25° C.). The resulting red solid is dissolved in a minimum amount of water, and precipitated by the addition of 3 g of ammonium hexafluorophosphate. The resulting red/orange solid is filtered, dried, and recrystallized from a mixture of methanol and acetonitrile yielding 620 mg of 68 as an red crystalline solid. NMR: $^{13}$C NMR (75 MHz, DMSO-d$_6$, DEPT (90) correlations) δ 123.727, 124.131, 127.694, 127.851, 128.896, 134.281, 137.282, 148.388, 148.388, 153.441, 157.456. FABMS Calcd. for C$_{25}$H$_{20}$N$_5$= 390.1719 Found=390.24.

EXAMPLE 10

Preparation of diaza Anthracene dimer: 7,18-bis (dimethylamino)-benzo[g]bispyrido[1',2':3,4] imidazo[1,5-a:5',1'-c]quinoxaline-6,17-diium bishexafluorophosphate 69

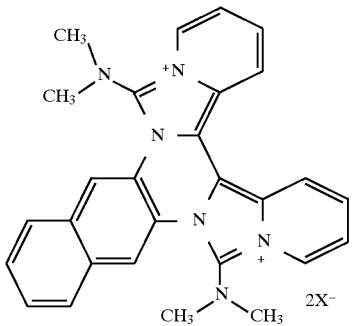

69

Thionyl chloride (10 mL) is added to a 25 mL round bottom flask in an ice bath. To the flask is added 664 mg (2.0 mmole) of 67, and the mixture stirred for 5 minutes. Dimethyl formamide (514 mg, 7.0 mmole) is added over a period of 20 minutes, and the orange solution stirred for 30 minutes. The thionyl chloride is removed under reduced pressure (~0.1 torr, 25° C.). The resulting red solid is dissolved in a minimum amount of water, and precipitated by the addition of 3 g of ammonium hexafluorphosphate. The resulting red solid is filtered, and recrystallized from a mixture of methanol (sparingly soluble) and acetonitrile (soluble), yielding 740 mg of 69 as a red crystalline solid. NMR: $^{13}$C NMR (100 MHz, DMSO-d$_6$).

EXAMPLE 11

Preparation of 6-(dimethylamino)-3,4-diphenyl-pyrido[1',2';3,4]imidazo[5,1-c]-1,2,4-triazine-5-ium perchlorate 71 (or 72)

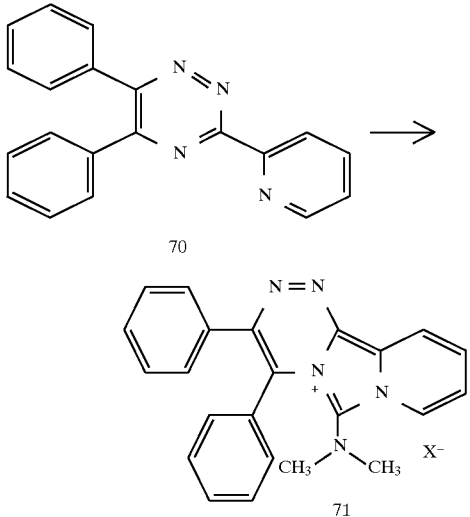

-continued

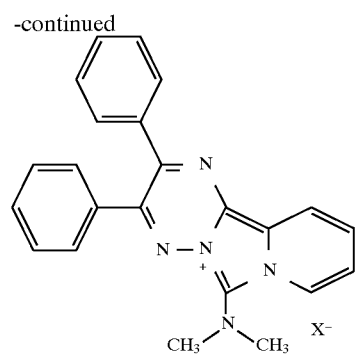

72

Thionyl chloride (10 mL) is added to a 25 mL round bottom flask in an ice bath. To the flask is added 620 mg (2.0 mmole) of 3-(2-pyridyl)-5,6-diphenyl-1,2,4-triazine 70, and the mixture stirred for 5 minutes. Dimethyl formamide (514 mg, 7.0 mmole) is added in a single portion, and the orange/red solution stirred for 30 minutes. The thionyl chloride is removed under reduced pressure (~0.1 torr, 25° C.). The resulting red solid is dissolved in a minimum amount of water, and precipitated by the addition of 3 g of ammonium hexafluorphosphate. The resulting red solid is filtered, and recrystallized from a mixture of methanol (sparingly soluble) and acetonitrile (soluble), yielding 690 mg of 71 or 72 as a red crystalline solid. 6-(dimethylamino)-3,4-pyrdio[1',2':3,4]imidazo[5,1-c][1,2,4]triazine-5-ium, diphenyl-perchlorate: $^1$H (300 MHz, DMSO-d6) δ 3.5 (s, 3H), 7.1 (m, 10H), 7.3 (m, 2H), 8.8 (m, 1H). $^{13}$C NMR (75 MHz, DMSO-d$_6$, DEPT (90) correlations) δ 40.77, 118.25, 1218.44, 118.68, 120.40, 120.96, 122.56, 126.08, 128.75, 129.03, 129.54, 129.76, 130.09, 130.47, 131.19, 134.27, 136.13, 146.71, 154.39.

EXAMPLE 12

A. Preparation of 3-(dimethylamino)-imidazo[1,5-a] pyridin-1-ol monoperchlorate salt 75

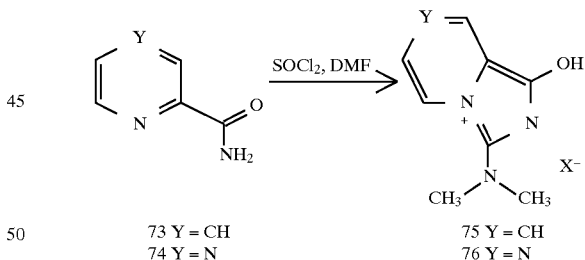

73 Y = CH
74 Y = N

75 Y = CH
76 Y = N

Thionyl chloride (10 mL) is added to a 25 mL round bottom flask in an ice bath. To the flask is added 800 mg (6.6 mmole) of 2-pyridine 73, and the mixture stirred for 5 minutes. Dimethyl formamide (1.02 g, 14 mmole) is added in a single portion, and the blue solution stirred for 90 minutes. The solvents are removed under reduced pressure to give 75 (1.0 g).

B. Preparation of Pyrazinamide adduct 76

Thionyl chloride (10 mL) is added to a 25 mL round bottom flask in an ice bath. To the flask is added 800 mg (6.5 mmole) of pyrazinamide 74, and the mixture stirred for 5 minutes. Dimethyl formamide (1.02 g, 14 mmole) is added in a single portion, and the blue solution stirred for 90 minutes. The solvents are removed under reduced pressure to give 76 (1.0 g).

EXAMPLE 13

A. Preparation of 2-Pyridinecarboxylic acid adduct 79

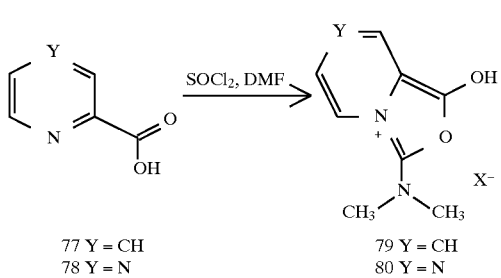

77 Y = CH
78 Y = N

79 Y = CH
80 Y = N

Thionyl chloride (10 mL) is added to a 25 mL round bottom flask in an ice bath. To the flask is added 800 mg (6.5 mmole) of 2-pyridinecarboxylic acid 77, and the mixture stirred for 5 minutes. Dimethyl formamide (1.02 g, 14 mmole) is added in a single portion, and the orange/red solution stirred for 90 minutes. The solvents are removed under reduced pressure to give 79 (0.600 g).

B. Preparation of 2-Pyrazinecarboxylic acid adduct 80

Thionyl chloride (10 mL) is added to a 25 mL round bottom flask in an ice bath. To the flask is added 800 mg (6.5 mmole) of 2-Pyrazinecarboxylic acid 74, and the mixture stirred for 5 minutes. Dimethyl formamide (1.02 g mg, 14 mmole) is added in a single portion, and the orange/red solution stirred for 90 minutes. The solvents are removed under reduced pressure to give 80 (0.900 g).

EXAMPLE 14

Preparation of 3-dimethylamino-imidazo [1,5-a] pyridine monoperchlorate 82

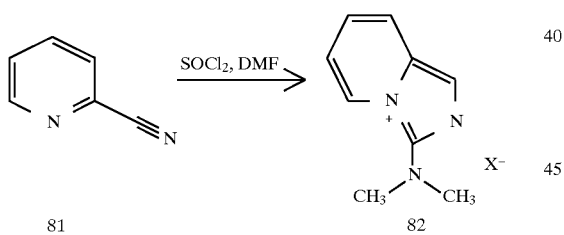

81

82

Thionyl chloride (25 mL) of cold (5° C.) is added to a 50 mL round bottom flask in an ice bath. To the flask is added 2.0 g (19.2 mmole) of 2-cyanopyridine 81, and the mixture stirred for 5 minutes. Dimethyl formamide (2.5 mg, 34.2 mmole) is added in a single portion, and the purple/blue solution stirred for 60 minutes. The thionyl chloride is removed under reduced pressure (~0.1 torr, 25° C.). The resulting blue solid is dissolved in a minimum amount of water, and precipitated by the addition of 7 g of magnesium perchlorate. The resulting blue solid is filtered, giving 1.5 g of 82 as a blue crystalline solid.

EXAMPLE 15

Preparation of 5-(carboxy)-12-(dimethylamino)-pyrido[1', 2':3,4]imidazo[1,5,a]quinlon-11-iumacyl chloride perchlorate 19 using POCl$_3$

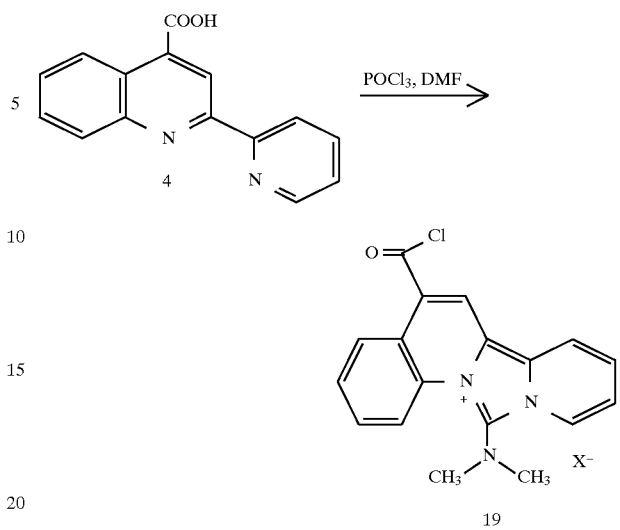

19

Phosphorous oxychloride (25 mL) is placed in a 50 mL round bottomed flask, fitted with a magnetic stirring bar, and cooled to 5°–10° C. While in an ice bath, with stirring, 1.0 g of 5 (4.2 mmol) is added. In a single portion, 530 mg (7.2 mmol) of DMF is added, producing an immediate color change. The orange solution is allowed to stir in the ice bath for 15 minutes. The ice bath is then removed and the solution is stirred for an additional 30 minutes. The phosphorous oxychloride is removed under reduced pressure, and the solid is dissolved in 100 mL of water. The solution is filtered, and 2 g of solid ammonium hexafluorphosphate is added, producing a bright yellow precipitate. The mixture is cooled to 5° C., and the solid filtered. The solid can be recrystallized from methanol giving the perchlorate salt 19 as a yellow solid (1.8 g). The $^1$H and $^{13}$C NMR data is exactly the same as the product derived from the SOCl$_2$ reaction.

EXAMPLE 16

Preparation of General Procedure of Fluorescent Cinchonic Acid Derivatives 20 using POCl$_3$ Phosphorous oxychloride (25 mL) is placed in a 50 mL round bottomed flask, fitted with a magnetic stirring bar, and cooled to 5°–10° C. While in an ice bath, with stirring, 1.1 g of 5 (4.2 mmol) is added. In a single portion, 530 mg (7.2 mmol) of N,N-dimethyl formamide (DMF) is added, producing an immediate color change. The orange solution is allowed to stir in the ice bath for 15 minutes. The ice bath is then removed and the solution is stirred for an additional 30 minutes. The phosphorous oxychloride is removed under reduced pressure, and the solid is dissolved in 100 mL of water. The solution is filtered, and 2 g of solid ammonium hexafluorphosphate is added, producing a bright yellow precipitate. The mixture is cooled to 5° C., and the solid filtered. The solid can be recrystallized from methanol giving the perchlorate salt 20 as a yellow solid (2.0 g).

EXAMPLE 17

Preparation of 3-dimethylamino-imidazo[1,5-a] pyridine monoperchlorate Using POCl₃

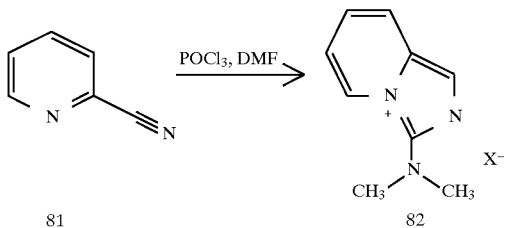

Phosphorous oxychloride (25 mL) is added to a 50 mL round bottom flask in an ice bath, and cooled to (5° C.). To the flask is added 2.0 g (19.2 mmole) of 2-cyanopyridine 81, and the mixture stirred for 5 minutes. Dimethyl formamide (2.5 mg, 34.2 mmole) is added in a single portion, and the purple/blue solution stirred for 60 minutes. The thionyl chloride is removed under reduced pressure (~0.1 torr, 25° C.). The resulting blue solid is dissolved in a minimum amount of water, and precipitated by the addition of 7 g of sodium perchlorate. The resulting blue solid is filtered, giving 2.2 g of 82 as a blue crystalline solid.

EXAMPLE 18

Preparation of Fluorescent PVA/Cinchonate Polymer 96

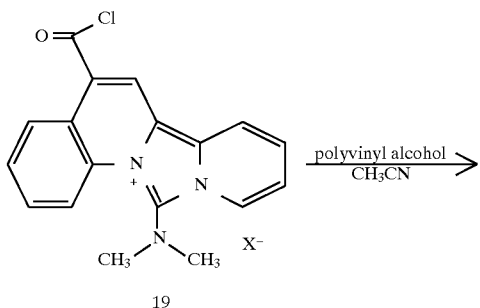

X = ClO₄, PF₆ or Cl

To a stirred mixture of 1.0 g of polyvinyl alcohol (MW 30,000–70,000) in 100 mL of acetonitrile is added 1.0 g (2.4 mmol) 19 (as its perchlorate salt). The mixture is stirred for 10 minutes, and then refluxed for 2 hours. The solid is filtered and washed with methanol (2×20 mL). The material is slightly soluble in hot water, and aqueous solutions can be evaporated to yield films of 96.

EXAMPLE 19

Preparation of Fluorescent 5-carboxy-12-(dibutylamino)-pyrido[1',2':3,4]-imidazo[1,5-a]quinolin-11-ium perchlorate 97 using N,N-dibutylformamide

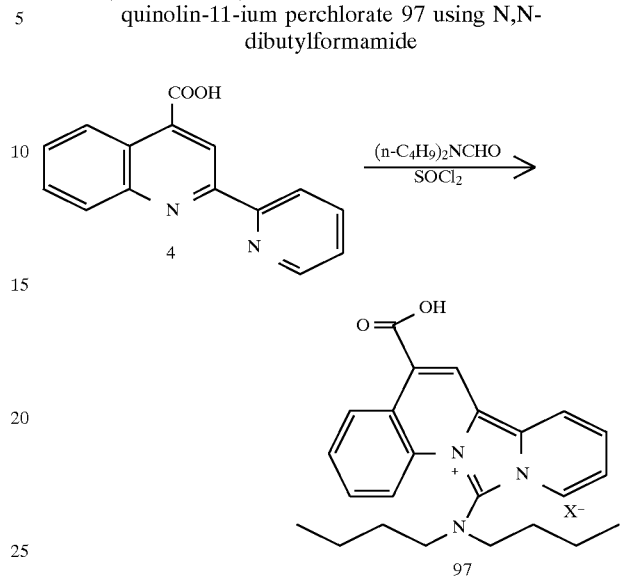

Thionyl chloride (25 mL) is placed in a 50 mL round bottomed flask, fitted with a magnetic stirring bar, and cooled to 5°–10° C. While in an ice bath, with stirring, 1.0 g of 4 (5.0 mmol) is added. In a single portion, 2.5 g (16 mmol) of N,N-dibutylformamide is added, producing an immediate color change. The orange solution is allowed to stir in the ice bath for 15 minutes. The ice bath is then removed and the solution is stirred for an additional 30 minutes. The thionyl chloride is removed under reduced pressure, and the solid is dissolved in 100 mL of water. The solution is filtered, and 2 g of solid ammonium hexafluorphosphate is added, producing a bright yellow precipitate. The mixture is cooled to 5° C., and the solid filtered. The solid can be recrystallized from methanol giving the perchlorate salts 97 as a yellow solid (1.8 g). 1H (300 MHz, DMSO-d₆) δ 0.78 (t, J=7.3 Hz, 6H), 1.15 (q, J=7.3, 4H), 1.55 (m, 4H), 3.75 (m, 4H), 7.55 (dd, J=6.8, 6.8 Hz, 1H), 7.60 (dd, J=6.8, 6.8 Hz, 1H), 7.85 (dd, J=8.0, 7.3 Hz, 1H), 7.95 (dd, J=7.3, 7.3 Hz 1H), 8.70 (d, J=6.8 Hz, 1H), 8.78 (d, J=8.6 Hz, 1H), 8.95 (d, J=8.0 Hz, 1H), 9.02 (s, 1H), 9.05 (d, J=8.6 Hz, 1H). ¹³C (DMSO-d₆) δ 14.00, 20.03, 30.50, 51.68, 116.93, 118.78, 119.21, 120.86, 122.34, 122.52, 123.46, 124.49, 126.19, 127.87, 129.27, 130.01, 130.33, 131.13, 166.93.

EXAMPLE 20

Preparation of 5-carboxy-12-(diethylamino)-pyrido[1',2':3,4]imidazo[1,5-a]quinolin-11-ium perchloate 98 using N,N-diethylformamide

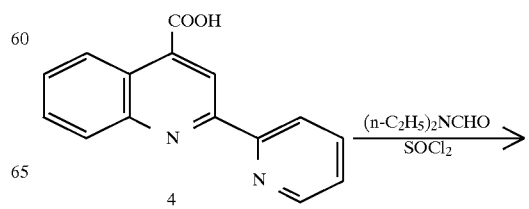

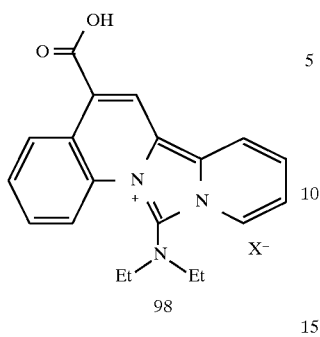

98

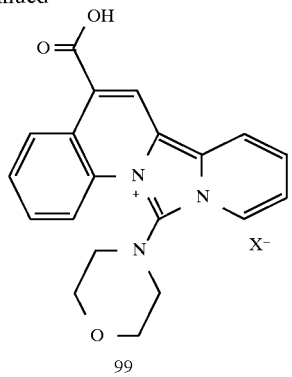

99

Thionyl chloride (25 mL) is placed in a 50 mL round bottomed flask, fitted with a magnetic stirring bar, and cooled to 5°–10° C. While in an ice bath, with stirring, 1.0 g of 4 (5.0 mmol) is added. In a single portion, 1.6 g (16 mmol) of N,N-diethylformamide is added, producing an immediate color change. The orange solution is allowed to stir in the ice bath for 15 minutes. The ice bath is then removed and the solution is stirred for an additional 30 minutes. The thionyl chloride is removed under reduced pressure, and the solid is dissolved in 100 mL of water. The solution is filtered, and 2 g of solid ammonium hexafluorphosphate is added, producing a bright yellow precipitate. The mixture is cooled to 5° C., and the solid filtered. The solid can be recrystallized from methanol giving the perchlorate salts 98 as a yellow solid (1.8 g). $^1$H (300 MHz, DMSO-$d_6$) δ 1.14 (t, J=7.1 Hz, 6H), 3.6 (m, 4H), 7.65 (dd, J=6.8, 6.8 Hz, 1H), 7.65 (dd, J=6.8, 6.8 Hz, 1H), 7.85 (dd, J=7.6, 7.6 Hz, 1H) 7.95 (dd, J=7.6, 7.6 Hz, 1H), 8.8 (d,J=6.8 Hz, 1H), 8.88 (d, J=8.6 Hz, 1H), 9.1 (s, 1H), 9.15 (d, J=8.6 Hz, 1H). $^{13}$C (DMSO-$d_6$) δ 13.91, 45.89, 117.05, 118.63, 119.32, 120.94, 122.43, 122.66, 123.57, 124.50, 126.29, 127.98, 129.33, 130.08, 130.36, 130.78, 166.91.

EXAMPLE 21

Preparation of Fluorescent 5-carboxy-12-(4-morpholinyl)pyrido[1',2':3,4]imidazo[1,5-a]quinolin-11-ium perchlorate

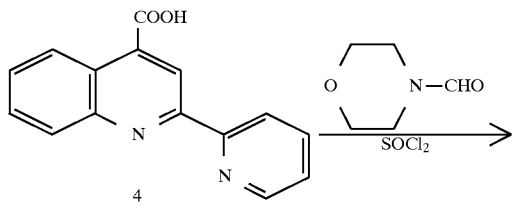

Thionyl chloride (25 mL) is placed in a 50 mL round bottomed flask, fitted with a magnetic stirring bar, and cooled to 5°–10° C. While in an ice bath, with stirring, 1.0 g of 4 (5.0 mmol) is added. In a single portion, 1.84 g (16 mmol) of 1-Morpholinecarboxyaldehyde is added producing an immediate color change. The orange solution is allowed to stir in the ice bath for 15 minutes. The ice bath is then removed and the solution is stirred for an additional 30 minutes. The thionyl chloride is removed under reduced pressure, and the solid is dissolved in 100 mL of water. The solution is filtered, and 2 g of solid ammonium hexafluorphosphate is added, producing a bright yellow precipitate. The mixture is cooled to 5° C., and the solid filtered. The solid can be recrystallized from methanol giving the perchlorate salts 99 as a yellow solid (1.4 g).

EXAMPLE 22

Preparation of 5-carboxy-12-(1-pyrrolidinyl)pyrido[1',2':3,4]imidazo[1,5-a]quinolin-11-ium perchlorate 100 using 1-pyrrolidinecarboxaldehyde

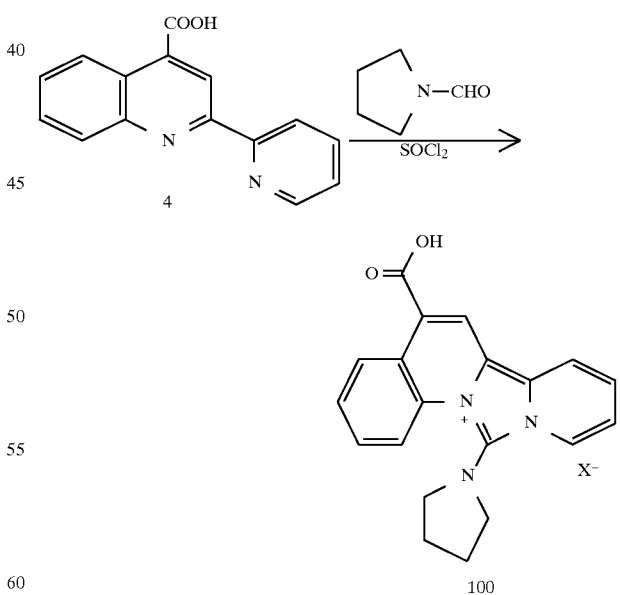

100

Thionyl chloride (25 mL) is placed in a 50 mL round bottomed flask, fitted with a magnetic stirring bar, and cooled to 5°–10° C. While in an ice bath, with stirring, 1.0 g of 4 (5.0 mmol) is added. In a single portion, 1.6 g (16 mmol) of 1-Pyrrolidinecarboxaldehyde is added, producing an immediate color change. The orange solution is allowed to stir in the ice bath for 15 minutes. The ice bath is then removed and the solution is stirred for an additional 30 minutes. The thionyl chloride is removed under reduced pressure, and the solid is dissolved in 100 mL of water. The solution is filtered, and 2 g of solid ammonium hexafluorphosphate is added, producing a bright yellow precipitate. The mixture is cooled to 5° C., and the solid filtered. The solid can be recrystallized from methanol giving the perchlorate salts 100 as a yellow solid (1.4 g). NMR: $^1$H (300 MHz, DMSO-d$_6$) 1.90 (m, 4H), 3.0 (m, 4H), 4.0 (s, 3H), 7.65 (m, 2H), 7.70 (t, J=?, 1H), 8.05 (t, J=?, 1H), 8.10 (t, J=?, 1H), 8.55 (d, J=?, 1H), 8.60 (d, J=?, 1H), 8.65 (m, 1H), 8.70 (s, 1H). $^{13}$C (DMSO-d$_6$) δ 24.02, 45.21, 53.44, 119.85, 123.06, 124.69, 125.65, 126.49, 129.72, 130.27, 131.27, 136.66, 141.51, 147.54, 148.18, 153.0, 153.5, 148.18, 166.27.

EXAMPLE 23

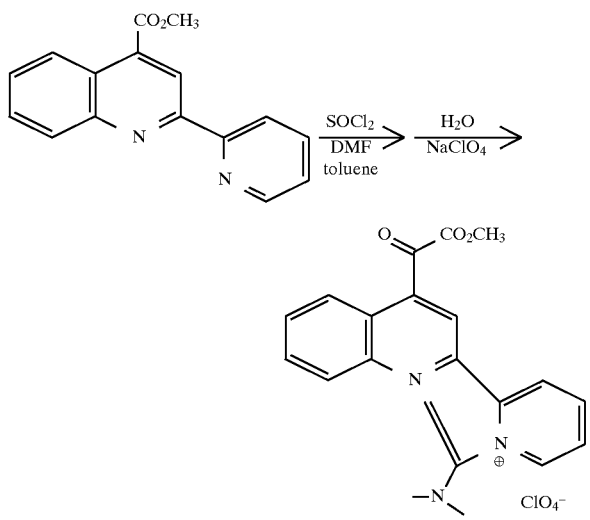

A 50-ml, one neck, round-bottomed flask is equipped with a stirring bar. The flask is charged with 1.00 g (3.78 mmol) of (4-carboxymethyl-2-(2-pyridyl)quinoline 5), and 5 Ml of toluene was added then cooled in ice water bath to 0° C. To this solution 10 equivalents (2.76 h, 2.972 mL, 37.8 mmol) of cold thionyl chloride is added and the cold solution immediately becomes yellow/orange. The solution is stirred in a well ventilated hood for an hour and allowed to warm to room temperature. The contents of the flask is then poured into a 100 mL beaker and placed in the well ventilated hood where the thionyyl chloride is allowed to evaporate overnight. The resulting red solid is dissolved in 50 mL of water and allowed to precipitate by the addition of 3 g (24.5 mmol) of sodium perchlorate. The resulting yellow solid was filtered and 1.,2 g (75.6%) of the fluorescent product is obtained. The compound can be recrystallized from acetonitrile or a mixture of methanol and acetonitrile. The $^1$H and $^{13}$C NMR spectra are identical to the product 21 obtained in Example 2.

EXAMPLE 24

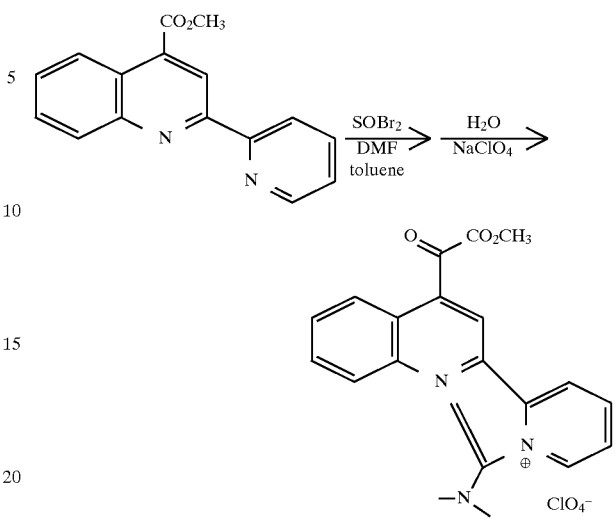

A 50-mL, one neck, round bottomed flask is equipped with a stirring bar. The flask is charged with 1.00 g (3.78 mmol) of 4-carboxymethyl-2-(2-pyridyl)quinoline 5) and 5 mL of toluene was added then cooled in an ice water bath at 0° C. To this solution 10 equivalents (2.76 g, 2.972 mL, 37.8 mmol) of dimethyl formamide is added. To this mixture, ice cold 5 equivalents (3.93 g, 1.38 mL, 18.9 mmol) of cold thionyl bromide is added and the cold solution immediately becomes dark red and a precipatate forms. The solution is stirred in a well ventilated hood for an hour and allowed to warm at room temperature. The contents of the flask is then poured into a 100 mL beaker and placed in the well ventilated hood where the excess thionyl bromide is allowed to evaporate overnight. The resulting red solid is dissolved in 50 mL of water and allowed to precipitate by the addition of 3 g (24.5 mmol) of sodium perchlorate. The resulting yellow solid was filtered and 0.8 g (50%) of two compounds is obtained. After performing an alumina column on the mixture we obtained the fluorescent product 20, similarly obtained in Example 2. The 1H and $^{13}$C NMR sspectra are identical to the product obtained in Example 2.

EXAMPLE 25

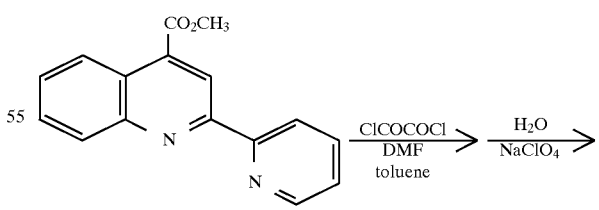

-continued

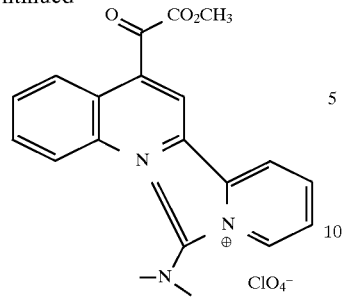

A 50-mL, one neck, round bottomed flask is equipped with a stirring bar. The flask is charged with 1.00 g (3.78 mmol) of (4-carboxymethyl-2-(2-pyridyl)quinoline 5) and 5 mL of toluene was then added, cooled in an ice water bath to 0° C. To this solution 10 equivalents (2.76 g, 2.927 mL, 37.8 mmol) of dimethyl formamide is added. To this mixture ice cold 1.5 equivalents (0.720 g, 0.487 mL, 5.67 mmol) of oxalyl chloride is added and the cold solution immediately becomes yellow/orange and a precipitate immediately forms at the bottom of the flask. The solution is stirred in a well ventilated hood for an hour and allowed to warm to room temperature. The remaining solution is then poured off and 5 mL of toluene is added and subsequently removed. The resulting red solid is dissolved in 50 mL of water and allowed to precipitate by the addition of 3 g (24.5 mmol) of sodium perchlorate. The $^1$H and $^{13}$C NMR spectra are identical to the product 21 obtained in Example 2.

EXAMPLE 26

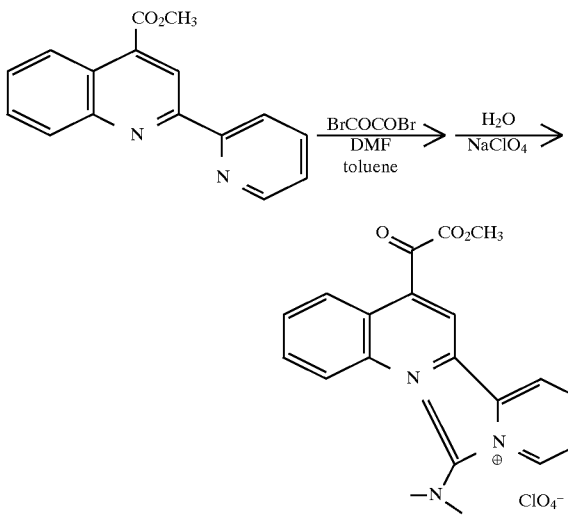

A 50-mL, one neck, round-bottomed flask is equipped with a stirring bar. The flask is charged with 1.00 g (3.78 mmol) of (4-carboxymethyl-2-(2-pyridyl)quinoline 5) and 5 mL of toluene was added, then cooled in an ice water bath to 0° C. To this solution 10 equivalents (2.76 g, 2.927 mL, 37.8 mmol) of dimethyl formamide is added. To this mixture ice cold 1.5 equivalents (0.4346 g, 0.288 mL, 5.67 mmol) of thiophosgene is added and the cold solution immediately becomes yellow/orange and a precipitate immediately forms at the bottom of the flask. The solution is stirred in a well ventilated hood for an hour and allowed to warm to room temperature. The remaining solution is then poured off, and 5 mL of toluene is added and subsequently decanted. The resulting solid is then dissolved in 20 mL of water and allowed to precipitate by the addition of 3 g (24.5 mmol) of sodium perchlorate. The $^1$H and $^{13}$C NMR spectra are identical to the product 21 obtained in Example 2.

EXAMPLE 27

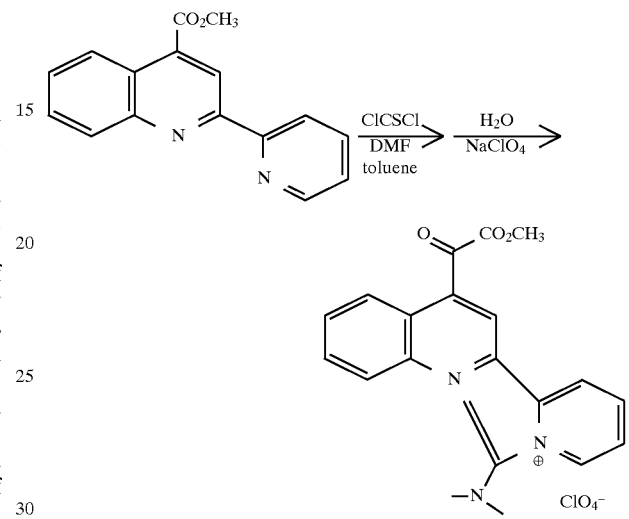

A 50-mL, one neck, round-bottomed flask is equipped with a stirring bar. The flask is charged with 1.00 g (3.78 mmol) of (4-carboxymethyl-2-(2-pyridyl)quinoline 5), and 5 mL of toulene was added, then cooled in an ice water bath to 0° C. To this solution 10 equivalents (2.76 g, 2.927 mL, 37.8 mmol) of dimethyl formamide is added. To this mixture ice cold 1.5 equivalents (0.4346 g, 0.288 mL, 5.67 mmol) of thiophosgene is added, and the cold solution immediately becomes yellow/orange and a precipitate immediately forms at the bottom of the flask. The solution is stirred in a well ventilated hood for an hour, and allowed to warm to room temperature. The remaining solution is then poured off and 5 mL of toluene is added and subsequently decanted. The resulting solid is then dissolved in 20 mL of water and allowed to precipitate by the addition of 3 g (24.5 mmol) of sodium perchlorate. The $^1$H and $^{13}$C NMR spectra are identical to the product 21 obtained in Example 2.

EXAMPLE 28

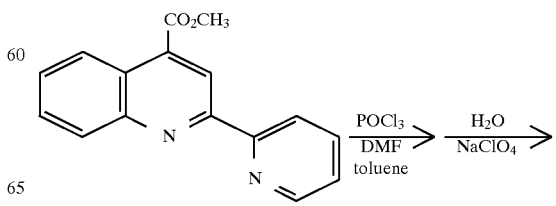

-continued

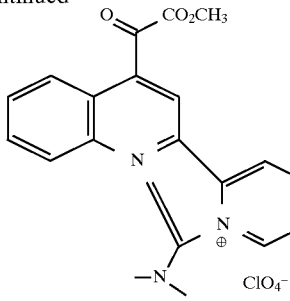

A 50-mL, one neck, round-bottomed flask is equipped with stirring bar. The flask is charged with 1.00 g (3.78 mmol) of (4-carboxymethyl-2-(2-pyridyl)quinoline 5), and 5 mL of toulene was added, then cooled in an ice water bath to 0° C. To this solution 10 equivalents (2.76 g, 2.927 mL, 37.8 mmol) of dimethyl formamide is added. To this mixture ice cold 10 equivalents 4.50 g, 2.76 mL, 37.8 mmol) of cold phosphoryl chloride is added and the cold solution immediately becomes yellow/orange. The solution is stirred in a well ventilated hood for an hour and allowed to warm to room temperature. The contents of the flask is then poured into a 100 mL beaker and placed in a well ventilated hood where the phosphoryl chloride is allowed to evaporate overnight. The resulting red solid is dissolved in 50 mL of water, and allowed to precipitate by the addition of 3 g (24.5 mmol) of sodium perchlorate. The title product can be recrystalized from acetonitrile or a mixture of methanol and acetonitrile. The $^1$H and $^{13}$C NMR spectra are identical to the product 21 obtained in Example 2.

EXAMPLE 29

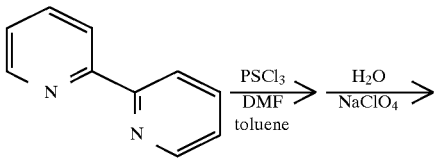

A 50-mL, one neck, round-bottomed flask is equipped with a stirring bar. The flask is charged 10 mL of toulene to which 1 mL (0.6079 g, 3.965 mmol) of phosphoryl chloride, and 5 equivalents (2.48 mL, 2.34 g, 32.0 mmol) of dimethyl formamide is then added. After the solution is stirred at room temperature for several minutes, 1.00 g (6.40 mmol) of 2,2'-bipyridine 35 is added and allowed to stir for five minutes. The solution is stirred in a well ventilated hood for an hour during which time the solution increasingly becomes a deep yellow color. The contents of the flask are then poured into a 100 mL beaker and placed in a well ventilated hood where the solution is allowed to evaporate overnight. The resulting yellow solid 41 that remains in the reaction flask is dissolved in 50 mL of water and allowed to precipitate by the addition of 3 g (24.5 mmol) of sodium perchlorate. The resulting yellow solid 41 was filtered and the NMR of this material confirmed the exclusive formation of the desired 6-(dimethylamino)dipyrido[1,2-c:2',1'-e] imidazol-5-ium-perchlorate (41) fluorescent adduct as previously shown in Example 4.

EXAMPLE 30

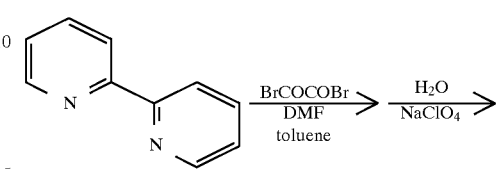

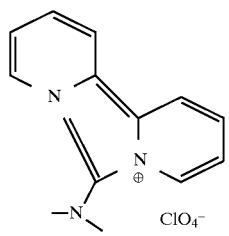

A 50-mL, one neck, round-bottomed flask is equipped with a stirring bar. The flask is charged with 1.00 g (6.40 mmol) of 2,2'-bipyridine, and cooled in an ice water bath, to which 2 equivalents (0.99 mL, 0.9360 g, 12.8 mmol) of ice cold oxalyl bromide is added and with the formation of a precipitate and a release of a gas is observed. The solution is stirred in a well ventilated hood for an hour. The contents of the flask are then filtered. The resulting brown solid is dissolved in 50 mL of water and allowed to precipitate by the addition of 3 g (24.5 mmol) of sodium perchlorate. The resulting yellow solid was filtered and the NMR of this material confirmed the formation of the desired dipyrido[1, 2-c:2',1'-e]imidazol-5-ium, 6-(dimethylamino),-perchlorate (41) fluorescent adduct as previously shown in Example 4.

EXAMPLE 31

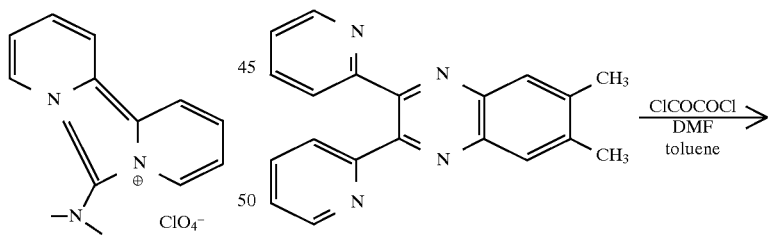

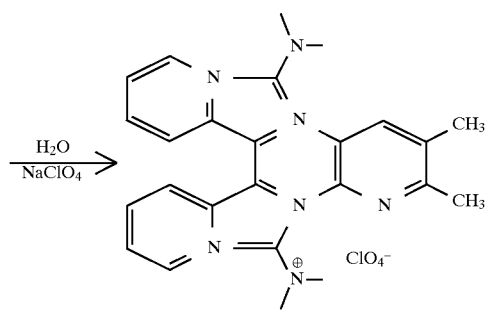

A 50-mL, one neck, round-bottomed flask is equipped with a stirring bar. The flask is charged with 1.00 g (3.20 mmol) of the substrate 2,3-dipyridyl-6,7-dimethyl-1,4,5-triazanaphthalene which is dissolved in 10 mL of toluene and cooled in an ice water bath, to which 5 equivalents (1.24 mL, 1.17 g, 16.0 mmol) of dimethyl formamide is added. The solution is allowed to cool, and 3 equivalentsdd (0.826 mL, 1.22 g, 9.60 mmol) of ice cold oxalyl chloride are then added and allowed stir for five minutes. When oxalyl chloride is added an immediate red precipitate is observed and a vigorous release of a gas is observed. The solution is stirred in a well ventilated hood for an hour. The solution of the flask is then poured into a 100 mL beaker and placed in a well ventilated hood where the solution is allowed to evaporate overnight. The resulting red solid is dissolved in 50 mL of water and is precipitated by the addition of 3 g (24.5 mmol) of sodium perchlorate. The resulting orange solid is filtered, and recrystalized from acetonitrile, yielding 1.25 g (63%) of one compound exclusively.

$^1$H (300 MHz, DMSO-d$_6$) δ 2.55(s, 6H), 3,25 (s, 12H), 7.39 (dd, J=7.0, 7.0 Hz, 2H), 7.53 (dd, J=9.5, 7.0 Hz, 2H), 8.06 (s, 2H), 8.45 (d, J=9.5 Hz, 1H), 8.63 (d, J=7.0 Hz, 1H). $^{13}$C NMR (75 MHz, DMSO-d$_6$, DEPT (90) correlations) δ 20.47 (CH$_2$), 40.13 (CH$_3$), 107.69 (C), 118.78 (CH), 1119.11 (CH), 120.08 (CH), 120.91 (C), 122.18 (C), 123.52 (CH), 127.07 (CH), 135.21 (C), 140.19 (C).

What is claimed is:

1. A compound of the formula

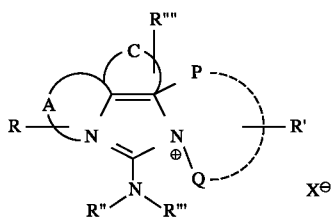 (I)

wherein A represents the atomic group necessary to form a heteroaromatic ring, which may be optionally substituted by one or more R substituents selected from the group consisting of aryl, heteroaryl, lower alkyl, hydroxy, halo, lower alkylamino, amino, nitro, or carboxy substituents;

wherein P or Q are optional substituents, each independently a substituent selected from the group consisting of aryl, heteroaryl, lower alkyl, hydroxy, halo, lower alkylamino, amino, nitro, or carboxy, or P and Q together represent the atomic group necessary to form a heteroaromatic ring, said P and Q substituents independently or together which may optionally be substituted by one or more R' substituents selected from the group consisting of aryl, heteroaryl, lower alkyl, hydroxy, halo, lower alkylamino, amino, nitro, or carboxy substituents;

C is an optional substituent which represents the atomic group necessary to form an aromatic or heteroaromatic ring, which may optionally be substituted by one or more R"" substituents selected from the group consisting of aryl, heteroaryl, lower alkyl, hydroxy, halo, lower alkylamino, amino, nitro, or carboxy substituents;

R" is hydrogen, a lower alkyl or aryl group, or together with R'" and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group;

R'" is a lower alkyl or aryl group, or together with R" and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group; and X is an anion.

2. A compound according to claim 1 wherein A is a quinolinyl group.

3. A compound according to claim 2 which is 5-carboxy-12-dimethylamino-pyrido[1',2':3,4]imidazo[1,5-a]quinolin-11-ium acyl chloride perchlorate, or another salt thereof.

4. A compound according to claim 2 which is 5-carboxy-12-dimethylamino-pyrido[1',2':3,4]imidazo[1,5-a]quinolin-11-ium perchlorate, or another salt thereof.

5. A compound according to claim 2 which is 5-methoxycarboxyl-12-dimethylamino-pyrido[1',2':3,4]imidazo[1,5-a]quinolin-11-ium perchlorate, or another salt thereof.

6. A compound according to claim 2 which is 5-methoxy-12-dimethylamino-pyrido[1',2':3,4]imidazo[1,5-a]quinolin-11-ium perchlorate, or another salt thereof.

7. A compound according to claim 2 which is 5-chloroethoxycarboxy-12-dimethylamino-pyrido[1',2':3,4]imidazo[1,5-a]quinolin-11-ium perchlorate, or another salt thereof.

8. A compound according to claim 2 which is 5-carboxy-12-dimethylamino-pyrido[1',2':3,4]imidazo[1,5-a]quinolin-11-ium 5(R)-methylbenzylamide perchlorate, or another salt thereof.

9. A compound according to claim 2 which is 5-carboxy-12-dimethylamino-pyrido[1',2':3,4]imidazo[1,5-a]quinolin-11-ium 5(S)-methylbenzylamide perchlorate, or another salt thereof.

10. A compound according to claim 2 which is 5-carboxy-12-diethylamino-pyrido[1',2':3,4]imidazo[1,5-a]quinolin-11-ium perchlorate, or another salt thereof.

11. A compound according to claim 2 which is 5-carboxy-12-dibutylamino-pyrido[1',2':3,4]imidazo[1,5-a]quinolin-11-ium perchlorate, or another salt thereof.

12. The compound according to claim 2 which is 5-carboxy-12-(4-morpholinyl)pyrido[1',2':3,4]imidazo[1,5-a]quinoline-1-ium perchlorate, or another salt thereof.

13. The compound according to claim 2 which is a 5-(amino acid)-12-dimethylamino-pyrido[1',2':3,4]imidazo[1,5-a]quinolin-11-ium perchlorate, or another salt thereof.

14. The compound according to claim 1 wherein A and the combination of P and Q each represent the atomic group necessary to form a pyridyl group.

15. The compound according to claim 14 which is 6-(dimethylamino)-dipyrido[1,2-c:2',1'-e]imidazol-5-ium perchlorate, or another salt thereof.

16. The compound according to claim 14 which is 6-(dimethylamino)-2,10-bis(carboxy)-dipyrido[1,2c-:2',1'-e]imidazol-5-ium perchlorate, or another salt thereof.

17. The compound according to claim 14 which is 6-(dimethylamino)-2,10-bis(methoxycarbonyl)-dipyrido[1,2c-:2',1'-e]imidazol-5-ium perchlorate, or another salt thereof.

18. The compound according to claim 14 which is 6-(dimethylamino)-2,10-bis(diethylaminocarbonyl)-dipyrido[1,2-c:2',1'-e]imidazol-5-ium hexafluorophosphate, or another salt thereof.

19. The compound according to claim 14 which is 6-(dimethylamino)-2,10-bis(2'-pyridyl)-dipyrido[1,2-c:2',1'-e]imidazol-5-ium hexafluorophosphate, or another salt thereof.

20. A compound according to claim 1 wherein A represents the atomic group necessary to form a pyrazine group and the combination of P and Q represents the atomic group necessary to form a pyridyl group.

21. The compound according to claim 20 which is 6-(dimethylamino)-1-(2-pyridinyl)-pyrido[1',2':3,4]imidazo[1,5-a]pyrazin-5-ium perchlorate, or another salt thereof.

22. A compound according to claim 1 wherein A represents the atomic group necessary to form a quinoxaline group and the combination of P and Q represents the atomic group necessary to form a pyridyl group.

23. The compound according to claim 22 which is 12-(dimethylamino)-6-(2-pyridinyl)-pyrido[1',2':3,4]imidazo[1,5-a]quinoxalin-11-ium perchlorate, or another salt thereof.

24. A compound according to claim 1 wherein A represents the atomic group necessary to form a diazaanthracene group and the combination of P and Q represents the atomic group necessary to form a pyridyl group.

25. The compound according to claim 24 which is 13-(dimethylamino)-7-(2-pyridinyl)-benzo[g]-pyrido[1',2':3,4]imidazo[1,5-a]quinoxaline-12-ium perchlorate, or another salt thereof.

26. A compound according to claim 1 wherein A represents the atomic group necessary to form a triazine group and the combination of P and Q represents the atomic group necessary to form a pyridyl group.

27. The compound according to claim 26 which is 6-(dimethylamino)-3,4-diphenyl-pyrido[1',2':3,4]imidazo[5,1-c]-1,2,4-triazine perchlorate, or another salt thereof.

28. A compound according to claim 1 which additionally contains a further N—C—C—N moiety which has reacted with another equivalent of the disubstituted formamide reactant.

29. The compound according to claim 28 which is 6,11-di(dimethylamino)bispyrido[1',2':3,4]imidazo[1,5-a:5',1'-c]pyrazin-5,1-diium diperchlorate, or another salt thereof.

30. The compound according to claim 28 which is 6,13-(dimethylamino)bispyrido[1',2':3,4]imidazo[1,5-a:5',1'-c]quinoxalin-5,12-diium diperchlorate, or another salt thereof.

31. The compound according to claim 28 which is 7,18-bis(dimethylamino)benzo[g]bispyrido[1',2':3,4]imidazo[1,5-a,1'-c]]quinoxaline:-6,17-diium perchlorate, or another salt thereof.

32. A process for the preparation of a compound of the formula

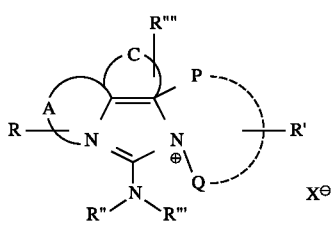

wherein A represents the atomic group necessary to form a heteroaromatic ring, which may be optionally substituted by one or more R substituents selected from the group consisting of aryl, heteroaryl, lower alkyl, hydroxy, halo, lower alkylamino, amino, nitro, or carboxy substituents;

wherein P or Q are optional substituents, each independently a substituent select from the group consisting of aryl, heteroaryl, lower alkyl, hydroxy, halo, lower alkylamino, amino, nitro, or carboxy, or P and Q together represent the atomic group necessary to form a heteroaromatic ring, said P and Q substituents independently or together which may optionally be substituted by one or more R' substituents selected from the group consisting of aryl, heteroaryl, lower alkyl, hydroxy, halo, lower alkylamino, amino, nitro, or carboxy substituents;

C is an optional substituent which represents the atomic group necessary to form an aromatic or heteroaromatic ring, which may optionally be substituted by one or more R"" substituents selected from the group consisting of aryl, heteroaryl, lower alkyl, hydroxy, halo, lower alkylamino, amino, nitro, or carboxy substituents;

R" is hydrogen, a lower alkyl or aryl group, or together with R"' and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group;

R"' is a lower alkyl or aryl group, or together with R" and the nitrogen atom to which it is attached, form a heterocyclic ring having from 5 to 7 members, which may optionally contain a sulfur, oxygen, silicon, selenium or an additional nitrogen atom, said ring optionally substituted with at least one lower alkyl group; and X is an anion, which comprises reaction of a compound of the formula II

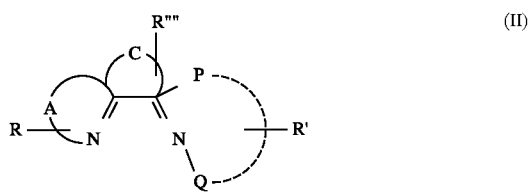

wherein A, C, P, Q, R, R' and R"" are as hereinbefore defined, with an N-substituted or N,N-disubstituted formamide of the formula III

wherein R" and R"' are as hereinbefore defined, in stoichiometric amounts, in the presence of a halogenating agent.

33. The process according to claim 32 wherein the halogenating agent is selected from the group consisting of thionyl chloride, thionyl bromide, phosphorus oxychloride, phosphorus tribromide, phosphorus triiodide, phosgene, phosphorus thiochloride, thiophosgene, oxalyl chloride, oxalyl bromide and phosphorus oxychloride.

34. The process according to claim 32 wherein the N,N-disubstituted formamide is N,N-dimethylformamide.

35. The process according to claim 32 wherein the reaction is conducted in a nonpolar aprotic solvent.

36. The process according to claim 32 wherein the reaction is conducted in a polar solvent.

37. The process according to claim 32 wherein the reaction is conducted under an inert atmosphere.

38. The process according to claim 32 wherein the react ant of Formula II contains a further N═C—C═N moiety which is reacted with another equivalent of the disubstituted formamide reactant to form a compound having an additional imidazolium ring.

39. A kit prepared using a fluorescent tag which comprises a compound of claim 1.

* * * * *